(12) United States Patent
Shachar et al.

(10) Patent No.: US 7,799,012 B2
(45) Date of Patent: Sep. 21, 2010

(54) MAGNETIC BREATHER PUMP AND A METHOD FOR TREATING A BRAIN TUMOR USING THE SAME

(75) Inventors: Yehoshua Shachar, Santa Monica, CA (US); Leslie Farkas, Ojai, CA (US); Bruce Marx, Ojai, CA (US); David Johnson, West Hollywood, CA (US); Laszlo Farkas, Ojai, CA (US); Thomas C. Chen, La Canada, CA (US)

(73) Assignee: Pharmaco-Kinesis Corporation, Inglewood, CA (US)

( * ) Notice: Subject to any disclaimer, the term of this patent is extended or adjusted under 35 U.S.C. 154(b) by 0 days.

(21) Appl. No.: 12/501,012

(22) Filed: Jul. 10, 2009

(65) Prior Publication Data
US 2009/0318903 A1 Dec. 24, 2009

Related U.S. Application Data

(62) Division of application No. 12/143,720, filed on Jun. 20, 2008.

(51) Int. Cl.
*A61M 31/00* (2006.01)
(52) U.S. Cl. ............... 604/508; 604/506; 604/507; 604/509; 604/890.1

(58) Field of Classification Search ............. 604/65–67, 604/101.01, 101.02, 103.01, 103.02, 131, 604/151–155, 257–258, 508, 890.1, 891.1, 604/892.1, 97.01, 97.02, 506, 507; 222/105, 222/207, 386.5, 527
See application file for complete search history.

(56) References Cited

U.S. PATENT DOCUMENTS

| | | | | |
|---|---|---|---|---|
| 4,360,019 A | * | 11/1982 | Portner et al. | 604/131 |
| 4,378,797 A | * | 4/1983 | Osterholm | 604/24 |
| 4,610,658 A | * | 9/1986 | Buchwald et al. | 604/9 |
| 5,429,582 A | * | 7/1995 | Williams | 600/2 |
| 6,810,290 B2 | * | 10/2004 | Lebel et al. | 607/60 |
| 2007/0135765 A1 | * | 6/2007 | Miller et al. | 604/131 |
| 2008/0064966 A1 | * | 3/2008 | Brockway et al. | 600/486 |

* cited by examiner

*Primary Examiner*—Kevin C Sirmons
*Assistant Examiner*—Larry R Wilson
(74) *Attorney, Agent, or Firm*—Marcus C. Dawes; Daniel L. Dawes

(57) ABSTRACT

A magnetically controlled pump is implanted into the brain of a patient and delivers a plurality of medicating agents at a controlled rate corresponding to the specific needs of the patient. The current invention comprises a flexible double walled pouch that is formed from two layers of polymer. The pouch is alternately expanded and contracting by magnetic solenoid. When contracted, a medicating agent is pushed out of the pouch through a plurality of needles. When the pouch is expanded, surrounding cerebral fluid is drawn into the space between the double walls of the pouch from which it is drawn through a catheter to an analyzer. Cerebral fluid drawn from the patient is analyzed. The operation of the apparatus and hence the treatment is remotely controlled based on these measurements and displayed through an external controller.

7 Claims, 20 Drawing Sheets

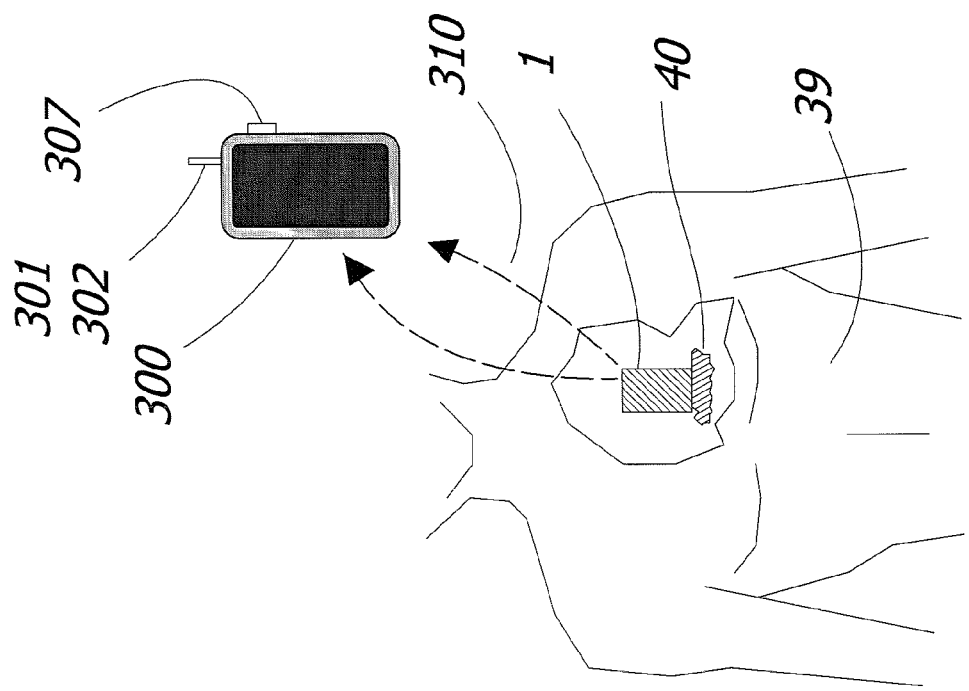
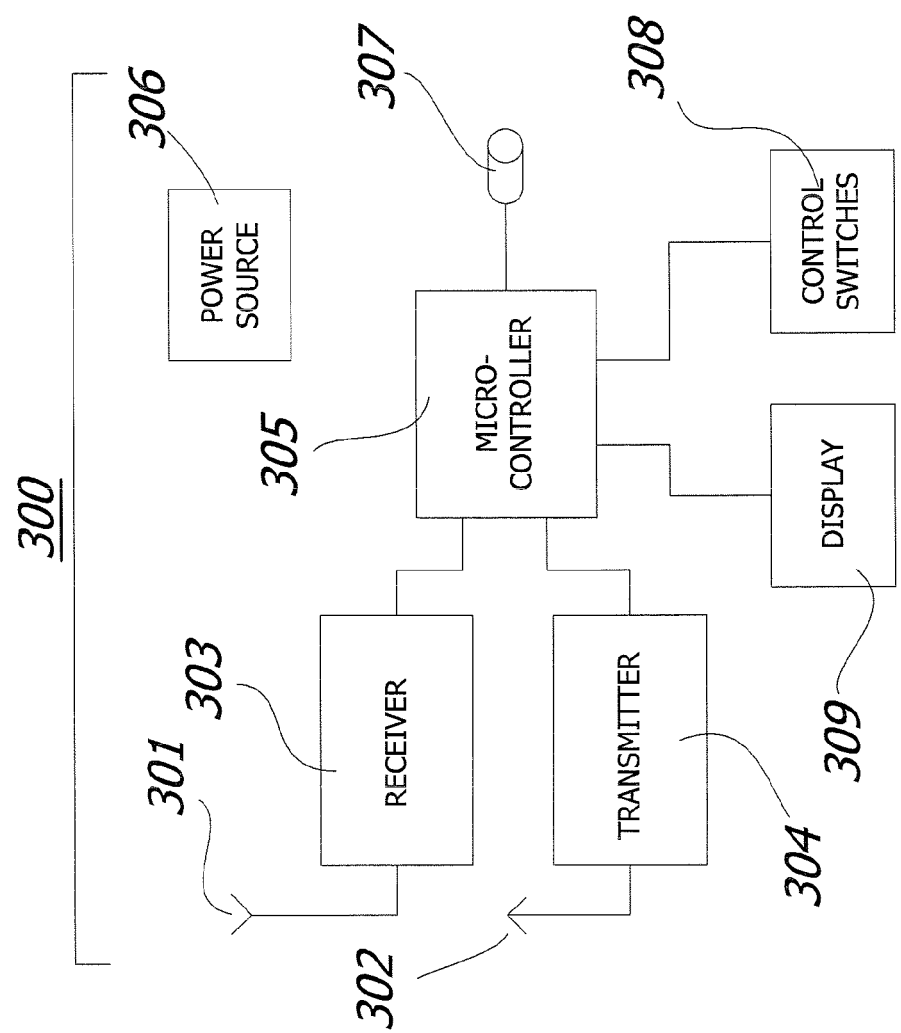
FIG. 1c
FIG. 1b

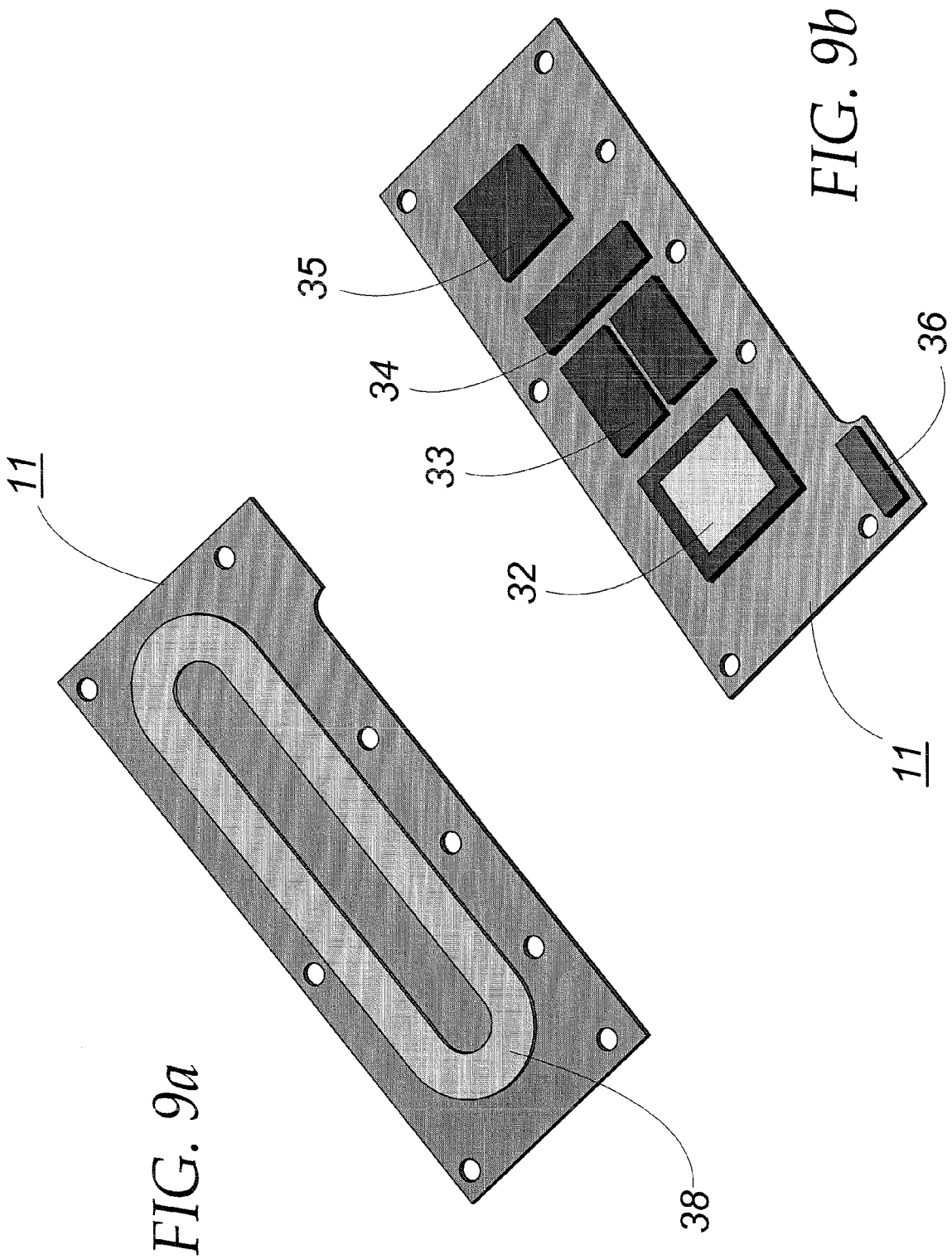

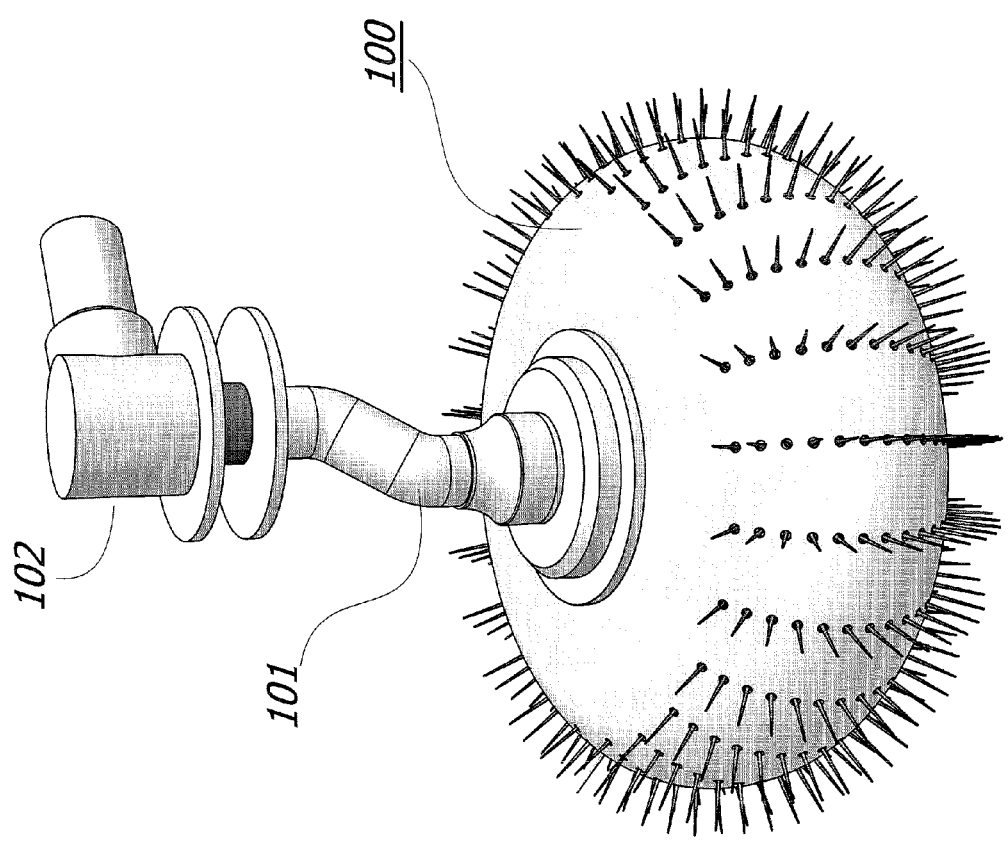

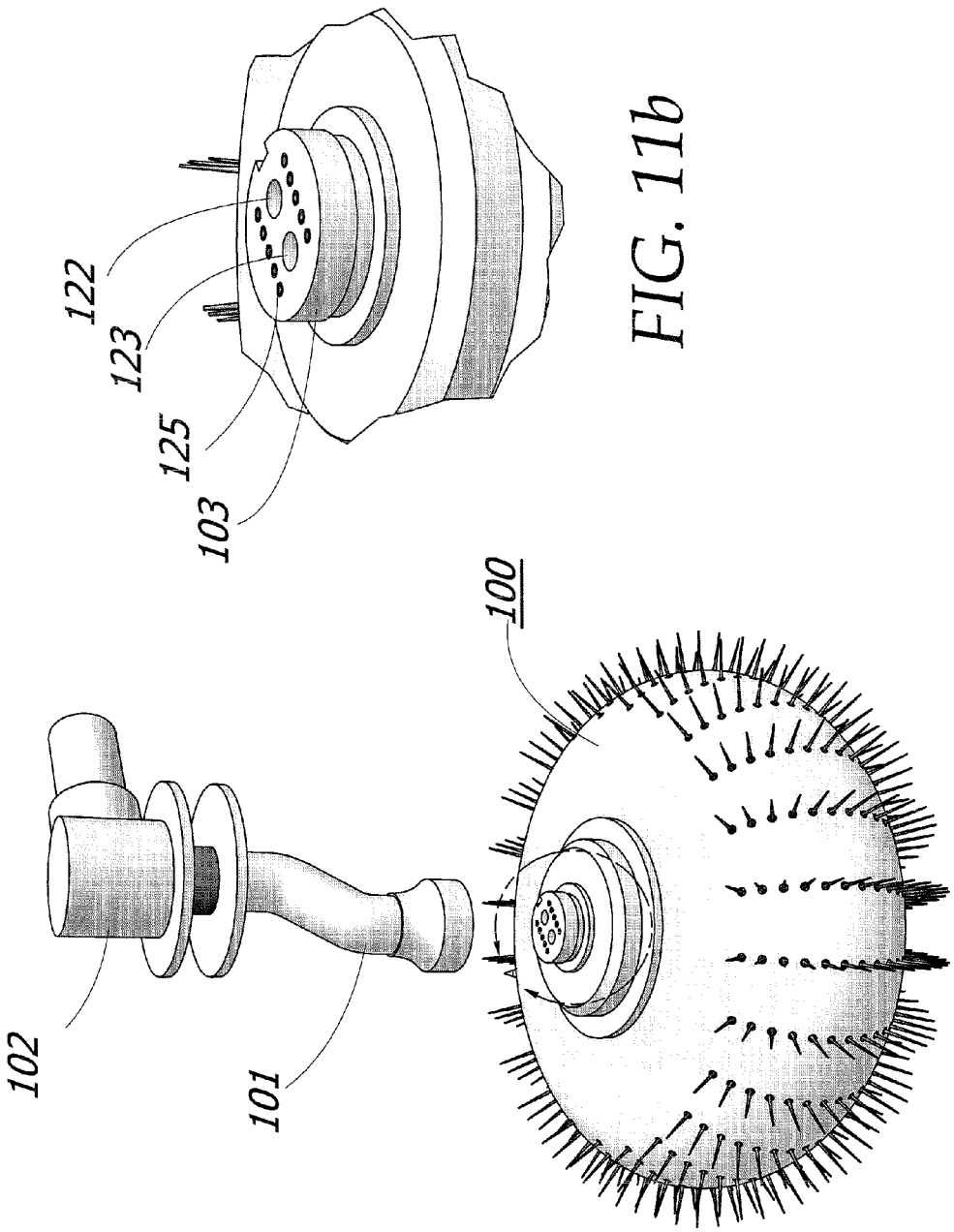

MAGNETIC BREATHER PUMP AND A METHOD FOR TREATING A BRAIN TUMOR USING THE SAME

RELATED APPLICATIONS

The present application is related to U.S. non-provisional application Ser. No. 12/143,720, filed Jun. 20, 2008, which is incorporated herein by reference and to which priority is claimed pursuant to 35 USC 120.

BACKGROUND OF THE INVENTION

1. Field of the Invention

The invention relates to the field of implantable drug delivery systems, specifically a magnetically controlled aspirating pump and a method for treating a brain tumor using the same.

2. Description of the Prior Art

When tumors develop inside the human body, the options for available treatment are fairly narrow. This is even more so when the tumor develops inside a vital organ such as the brain. Diseases such as brain cancer, i.e. malignant gliomas, and other maladies that develop in or around the brain are notoriously difficult to treat and thus have a high mortality rate. The invention described herein is directed specifically for malignant gliomas; however, it is applicable to all types of malignant brain tumors.

Traditionally, the options for treating a tumor located in or on the brain include surgery, radiation, chemotherapy, and local intratumoral therapy. Each of these prior methods of treating a brain tumor have had some form of success in the past, however each of them also contain various deficiencies and pitfalls that make them less than ideal when treating a patient. What is needed is a more reliable, easier, and effective process for treating a malignant brain tumor.

The oldest and most direct way for treating a brain tumor is to remove it surgically. Surgery is effective in obtaining tissue diagnosis and removing the mass effect of the tumor from the adjacent normal brain. However, it is invasive, expensive, and poses potential surgical complications for the patient. Most importantly, surgery cannot cure a malignant brain tumor, as the cancer cells have often invaded far into the normal brain when the diagnosis is first confirmed. Additionally, surgery is only available when the tumor is in a surgically accessible location. Tumors located deep within the brain are often inoperable as the surgery would significantly impair the patient's neurological function. Even if surgery is possible, there is still a chance of brain damage and an extremely long recovery time associated with surgery.

Radiation is the next mode of treatment for brain cancer. It is usually given as a fractionated dosage treatment, covering a certain field encompassing the tumor, over a period of six weeks. Spatially localized forms of radiation, including cyberknife and gamma knife have been used with varying levels of success. Although radiation is still widely acknowledged as the most effective mode of adjunctive treatment for a malignant brain tumor, it suffers from the disadvantage of limited fractions and applications, as the brain can only be radiated so much without developing severe sequelae.

The third method used to combat brain tumors is systemic chemotherapy. Systemic chemotherapy is a viable option as an adjunct to radiation and surgery. However, it is limited in efficacy in brain cancers by: 1) delivery across the blood brain barrier, 2) development of drug resistance by the cancer cells, and 3) systemic side-effects from the chemotherapeutic agent. Because the blood brain barrier is only partially broken down in the presence of a malignant brain tumor, it still impairs the effective delivery and transport of systemic chemotherapy into the brain cancer. Secondly, brain tumors can develop drug resistance. As a result, the cancer learns how to avoid cytotoxicity of the delivered drug. Lastly, chemotherapy is distributed systemically throughout the entire body. Because the whole body of the patient undergoes the treatment (not just the tumor and the tumor related area), undesirable side effects such as nausea, diarrhea, hair loss, and loss of appetite and energy may occur. Some of the side effects are so strong in some patients that chemotherapy is unavailable to them as a treatment and thus decrease their overall chances for survival.

The last major method of treating brain tumors has been the application of various local intratumoral therapies. These therapies include chemotherapy wafers, stereotactic injections, and convection enhanced deliveries. All of these treatment therapies involve directly infusing the tumor with an appropriate drug regimen; however this method too is not without its limitations. Chemotherapy wafers (Gliadel) are currently limited by only one drug available (BCNU), and by its diffusion capability of only a few millimeters away from the tumor bed. Stereotactic injections of chemotherapy have also been applied. However, only one injection is available at any single time. If another injection is needed, then another stereotactic surgical injection would have to be performed. Moreover, the spread of the chemotherapy is limited to the injection site and some of the adjacent normal brain. Lastly, convection enhanced delivery via an external micropump has been used to increase the circumference of drug delivery. It is usually given by an externalized catheter, and the drug is delivered for a cycle of 4-6 days. At the end of that time, the catheter will have to be removed. If the drug is to be delivered again, another surgical procedure for convection enhanced delivery will have to be performed. This can be very expensive and painful as some intratumoral therapies involve exposing the brain to an externalized catheter for long periods of time or complicated implantations of temporary catheters and other medical devices. Additionally, many of the previous intratumoral therapies are ineffective and do not significantly enhance or lengthen the life of a patient receiving such treatment.

The underlying hypothesis of using polypharmacy employed by the current invention is based on cytotoxic drug is that more is better. Thus, a first step in administrating a cytotoxic agent is to determine the maximum tolerated dose (MTD). However, when used in traditional treatment mores, such as chemotherapy, the cytotoxic agents are delivered to the patient in a manner that allows the cytotoxic agents to be distributed more or less globally throughout the body of the patient. Relatively large doses of the drugs are required since only a small fraction of the administered dose will be present at the tumor site at any given time. The remainder of the dose will be in the other parts of body. Moreover, a major problem with conventional chemotherapy is lack of specifically targeting the cancer cell.

The use of large doses of toxic agents often leads to serious and debilitating side effects. Moreover, the global administration of drugs is often not compatible with combination therapies where a number of medicating agents are used synergistically to treat tumors or other conditions. Thus, the global administration of medicating agents to treat tumors and other such medical conditions is an inefficient and often dangerous technique that often leads to severe or debilitating side effects.

Recently, there have been some developments in the field of medical drug delivery systems. The majority of these systems have taken the form of a pump or other device that releases a variety of drugs into various positions in and around the body of a patient.

For example, many of the devices found in the prior art are much like the inventions disclosed in U.S. Pat. No. 6,852,104 ("Blonquist") and U.S. Pat. No. 6,659,978 ("Kasuga"). Both of these inventions comprise a small tank for holding a drug regimen, a pump for pumping the drug regimen into the body of a patient, and some sort of electronic control system that allows the user to program the specific amount and at what time a certain drug regiment is to be administered. While these apparatus may be ideal for administering certain drugs such as insulin to patients who are diabetic, they are neither designed nor suitable for directly treating a tumor within the brain of a patient.

Other prior art examples such as U.S. Pat. No. 5,242,406 ("Gross") and U.S. Pat. No. 6,571,125 ("Thompson") offer smaller, more convenient alternatives for administering drugs, however their reliance on maintaining a specific set of pressures and a certain amount of electrical current respectively makes them too complicated and prone to error.

U.S. Pat. No. 7,351,239 ("Gill"), U.S. Pat. No. 7,288,085 ("Olsen"), and U.S. Pat. No. 6,726,678 ("Nelson") disclose a pump or reservoir that is capable of delivering medicating fluids to the brain, but requires that the pump and drug reservoir be implanted in different locations within the patient. This configuration is not only uncomfortable for the patient, but also increases the possibility of infection and unnecessarily complicates the implanting procedure. Additionally, every time the patient needs the drug reservoir refilled or the pump battery replaced, the physician must invasively re-enter the patient. Finally, none these prior methods disclose a way of measuring the value of the vascular endothelial growth factor (VEGF) so as to enable tailoring of the delivered medical agent, toxicity to meet the needs of a specific individual patient.

What is needed is a device and a method that is capable of delivering medicating agents directly to a tumor located in the brain of a patient that is easy to operate and relatively simple to implant, while at the same time, is easy to maintain throughout the patient's treatment cycle and customize to the patient's specific needs without causing all of the negative side effects associated with previous treatment methods.

BRIEF SUMMARY OF THE INVENTION

A magnetically controlled pump is implanted into the brain of a patient and delivers a plurality of medicating agents at a controlled rate corresponding to the specific needs of the patient. The current invention comprises a flexible double walled pouch that is formed from two layers of polymer. The pouch is alternately expanded and contracting by magnetic solenoid. When contracted, a medicating agent is pushed out of the pouch through a plurality of needles. When the pouch is expanded, surrounding cerebral fluid is drawn into the space between the double walls of the pouch from which it is drawn through a catheter to an analyzer. Cerebral fluid drawn from the patient is analyzed. The operation of the apparatus and hence the treatment is remotely controlled based on these measurements and displayed through an external controller.

The illustrated embodiment of the invention solves the above limitations in the prior art and other problems by effectively treating brain tumors using a magnetically controlled pump implanted into the tumor resection cavity or a multi-delivery catheter implanted into an unresectable tumor, i.e. a tumor in which a surgical removal of all or part of an organ, tissue, or structure is not practically feasible. Through both proximal ports, an internalized externally controlled pump will deliver up to four different kinds of chemotherapeutic agents at a controlled rate corresponding to the specific needs of the patient.

The microdelivery pump has three components: a proximal head implanted into the tumor, a catheter extending from the proximal head, and an analyzer unit connected to the catheter. The proximal head is either comprised of a catheter inserted into the tumor or a magnetic breather pump. Which type of proximal head is employed depends on whether a tumor cavity is available. If a tumor is considered unresectable or if the patient does not want open surgery, only a catheter only will be implanted. However, if a resection is performed, then different size magnetic breather pumps can be inserted into the tumor cavity, depending on its volume. The entire unit is self-contained and entirely internalized.

Briefly, the illustrated embodiment of the invention comprises a proximal delivery device which will be implanted into the patient's brain tumor. A first embodiment is made for patients who have had a surgical resection, with a resultant tumor cavity. In those cases, a small, round flexible pouch that is formed from two layers of polymer material is implanted. At the head and base caps of the pouch are electromagnetic coils that, when activated, are alternately attracted and repelled from each other thus causing the pouch to contract and expand. The inner layer of polymer material acts as a reservoir for a medicating agent or a mixture of several medicating agents. The inner layer also contains a plurality of polymer needles on its surface that allow the medicating agent to pass through the outer polymer layer and deep into the surrounding tissue of the patient, when the pouch is contracted by the electromagnetic coils. The outer polymer layer is porous which allows surrounding cerebral fluid to be drawn into the pouch from the suction that is created when the pouch is expanded by the electromagnetic coils. This mechanical aspiration and exchange of fluids by the pouch is then repeated until the entire amount of medicating agent has been delivered, or until a preselected time period has expired.

The head cap of the pouch also contains a valve that allows the reservoir of the apparatus to be refilled and for cerebrospinal fluid that has been drawn into the pouch to be withdrawn from the cranium of the patient via a suction nozzle. In this way, the pump also enables a decompressive mechanism for controlling the intratumoral pressure, and for sampling fluid.

In patients in whom a resection cannot be performed, an alternative embodiment of the current invention involving a multidelivery catheter is employed. Conventional catheters used for convection enhanced delivery for brain tumors consist of either a single port in the tip of peritoneal tubing used for ventriculoperitoneal shunts, or a proximal shunt catheter with multiple holes cut within 1 cm of the tip of catheter tip. The multidelivery catheter described herein is comprised of a catheter tip from which a balloon with multiple spines emerges under positive pressure from the pump.

The medication intake line and the cerebrospinal fluid return line coupled to the head cap of the apparatus are housed within a silicone catheter. The catheter runs underneath the scalp of the patient, around the back of the head, and emerges from the patient in an easily accessible location such as beneath the head of the clavicle as in a portacath. The catheter is coupled to an analyzer unit, thus coupling the aspirating pump to a control device and forming a drug delivery system.

The analyzer unit is a housing means for several key components of the apparatus. Cerebrospinal and/or tumor fluid that has returned from the patient passes through a lab-on-a-chip which measures and monitors the vascular endothelial growth factor (VEGF) levels for indications of progress or regression of the patient's tumor burden. The user or physician operating the apparatus can then adjust or change the drug regimen the patient is receiving based on these measurements. Also coupled to the unit are four piezo pumps that send up to four different medicating agents through the catheter and into the reservoir of the implanted pouch. A Blue Tooth® chip also allows the unit to be controlled by a physician from a remote location. Flash memory chips and an artificial intelligence processor complete the circuitry needed in order to provide the patient with an effective, easy to use apparatus that delivers medicating agents at a set and controlled rate. Finally, the analyzer unit or chemotherapy pumping device (CPD) includes a long lasting lithium ion battery that powers the unit itself.

It is therefore an object of the invention to provide a patient with constant medication without re-implanting a catheter every time a patient needs to be treated.

It is another object of the invention to provide a metronomic continuous delivery of a medicating agent.

It is a further object of the invention to provide users and physicians in charge of a patient's treatment instant monitoring and feedback of various tumor parameters in order for the patient's treatment to be changed or adjusted accordingly.

It is a further object of the invention to provide patients with brain tumors an effective way of treating their affliction while minimizing the side effects of chemotherapy.

Another object of the invention is to enhance the mechanism of vectorial change of tumor escape mechanism by introducing a sufficient tumor antigen to stimulate the immune system of the patient.

Another object of the invention is to assist in irrigating the solid tumor by increasing cell adhesion molecules which are used for the adherence of cytotoxic cells to target cells before lysis can ensue. The malignant cells cannot bind to cytotoxic cells. The use of the apparatus will improve and enhance such a process.

Yet another object of the invention is to administrate biological response modifiers (BRMs) with an improved dose, local delivery and scheduling on a case-specific basis using the programmable microcontroller and its associated valve mechanism.

Another object of the invention is to allow the clinician the ability to prescribe an optimal biological dose (OBD) as opposed to maximum tolerated dose (MTD) by the use of an apparatus control mode defined by its programmability and its logic, which is embedded in microcontroller look-up-tables.

Another object of the invention is to incorporate the pharamacokinetic and pharmacodynamic parameters associated with chemotherapeutic agents so as to achieve the desired results without the toxic side effects known to those familiar with the art.

Another object of the invention is to modulate and modify the output of the medicating agents during treatment by changing the procedure in real time through the use of the command structure of the microcontroller look-up-tables with the use of a communication link built into the apparatus.

Another object of the invention is to regulate the rate of dispensation of the medicating agents by modifying the duty cycle of the valve located in the apparatus.

Another object of the invention is to regulate the intake of the tumor BRMs due to their pleiotropic nature, and allow for processes and mechanisms to develop by reducing or enhancing the various agents in the medicating apparatus (MBP), hence providing a treatment specific to the patient (e.g. tumor, size, lysis, etc).

Another object of the invention is to control and regulation capabilities to provide actions specific on a time domain such as the introduction of interferon alpha to tumor site (INF) whose immune modulating effects and/on anti-proliferate effects and dosing can be very different depending on which effect is to be maximally stimulated.

Another object of the invention is to provide maximum dosing of chemotherapeutic agents to the tumor site by using the maximum tolerated does (MTD) on a time domain which does not interfere with the activity of BRMs through the use of the selective control of the valve actuating mechanism built in the apparatus.

Another object of the invention is to provide the clinician a way to allow the expression of BRMs cascade effects (due to the communication of cytokines as messengers with their synergistic, additive or antagonistic interactions that affect the target tumor cells).

Another object of the invention is to provide scheduling of medicating agents such as chemotherapy and BRMs as based on their toxicity, and to allow for measures such as bioavailability, solubility, concentration, and circulation based on locality, both of which are the improved approach to the elimination of solid tumors.

Another object of the invention is to address the individual differences of various tumors based on the disease stage, immune factors, body weight, age and chronobiology through the ability of the apparatus to locally administer the agents, dosing, and scheduling.

Another object of the invention is to mitigate the known factors such as peak serum concentration, (generally associated with peak occurrence of side effects on interferons (IFN) intravenously injected, which serves as a typical model) whereby the peak concentration of IFN correlated clinically with peak side effects.

Another object of the invention is to support clinical studies and to demonstrate that responses to BRMs such as IFN-gamma follow a bell shaped response curve whereby when the concentration of the drug increases so does its response, hence the availability of apparatus with its local administration of drug delivery affords an improved use of such processes.

Another object of the invention is to provide an effective mode of administrating BRMs with chemotherapy as a combination therapy by making available a local administration of different IFNs with IL-2 or IL-2 in combination with monoclonal antibodies and tumor necrosis factors (TFNs), and scheduling by the use of the invention under metromonic regiment.

Another object of the invention is to enable drug manufacturers to evaluate the effectiveness of its drug during animal and clinical studies by providing the details and feedback on the use, dose, cycle, circadian time effects and the entire pharmacokinetic and pharmacodynamic behavior of the medicating agents not as verbal reports of symptomalogy chronicles by the patient, but as a biological measure of tumor responses to the agents.

Another object of the invention is to provide a method and apparatus for local administration of BRMs and chemotherapeutic agents, to enhance mechanisms that support overlapping effects in reducing tumor burden and elimination of tumors. To induce an improved response by the use of biomodulators (augmenting the patient's anti-tumor response via production of cytokines), decreasing suppressor mechanisms, increasing the patient's immunological response, limiting the toxicity of such agents (by the locality), maximizing the dose, increasing susceptibility of cells membrane characteristics for improved chemotherapy results at the site, and decreasing the tumor's ability to metastasize.

The above characteristics are measurable elements since dosing and scheduling improves the effectiveness of chemotherapy on malignant cells and reduces the exposure of such toxins to normal tissues. One embodiment provides improved immunomodulation with relatively little immuno-suppression.

Another object of the invention can be used by a variety of clinical techniques such as the Creech technique of regional or isolated limb perfusion to administer high-doses of chemotherapy to an isolated site of melanoma or sarcoma. This technique is used by BRMs and TNF-α have anti-tumor effects by damaging the neovascular circulation surrounding tumors without destroying normal tissue. The fact that the effective use of TNF-α cannot be administered systemically due to its toxic effects (septic shock) is one example of many that could have been cited from the variety of cytotoxic as well as chemotherapeutic agents. Hence the use of local administration by the illustrated embodiment is broadly beneficial.

Another object of the invention is to provide for defining an improved dose and schedule of biological agents to maximize the anti-tumor effects of each agent while not increasing toxicity to the patient. Treatment modality by the use of combination therapy and local administration of such agents on a specific schedule is one of the benefits of the invention.

Finally, it is yet another object of the invention to provide operating physicians a method of treating brain tumors without having to worry about medicating agents being diluted or hindered by the blood brain barrier (i.e. direct antibody injection into the tumor).

While the apparatus and method has or will be described for the sake of grammatical fluidity with functional explanations, it is to be expressly understood that the claims, unless expressly formulated under 35 USC 112, are not to be construed as necessarily limited in any way by the construction of "means" or "steps" limitations, but are to be accorded the full scope of the meaning and equivalents of the definition provided by the claims under the judicial doctrine of equivalents, and in the case where the claims are expressly formulated under 35 USC 112 are to be accorded full statutory equivalents under 35 USC 112. The invention can be better visualized by turning now to the following drawings wherein like elements are referenced by like numerals.

BRIEF DESCRIPTION OF THE DRAWINGS

FIG. 1b is a block diagram of the architecture of the external control unit which communicates with the implanted apparatus.

FIG. 1c is a diagram which illustrates the implantable pouch and its associated communications controller.

FIG. 4b is a magnified view of the delivery connector of FIG. 4a.

FIG. 9a is a perspective view of the top of the induction charger assembly.

FIG. 9b is a perspective view of the bottom of the induction charger assembly.

FIG. 10a is an isometric view of the implantable cranium pump.

FIG. 11a is an isometric view of the implantable cranium pump with the pump-to-seal interconnect disconnected.

FIG. 11b is a magnified view of the pump head assembly.

FIG. 13b is a magnified view of the injector spines in the circled region 13a of FIG. 13a.

The invention and its various embodiments can now be better understood by turning to the following detailed description of the preferred embodiments which are presented as illustrated examples of the invention defined in the claims. It is expressly understood that the invention as defined by the claims may be broader than the illustrated embodiments described below.

DETAILED DESCRIPTION OF THE PREFERRED EMBODIMENTS

Figure 12:
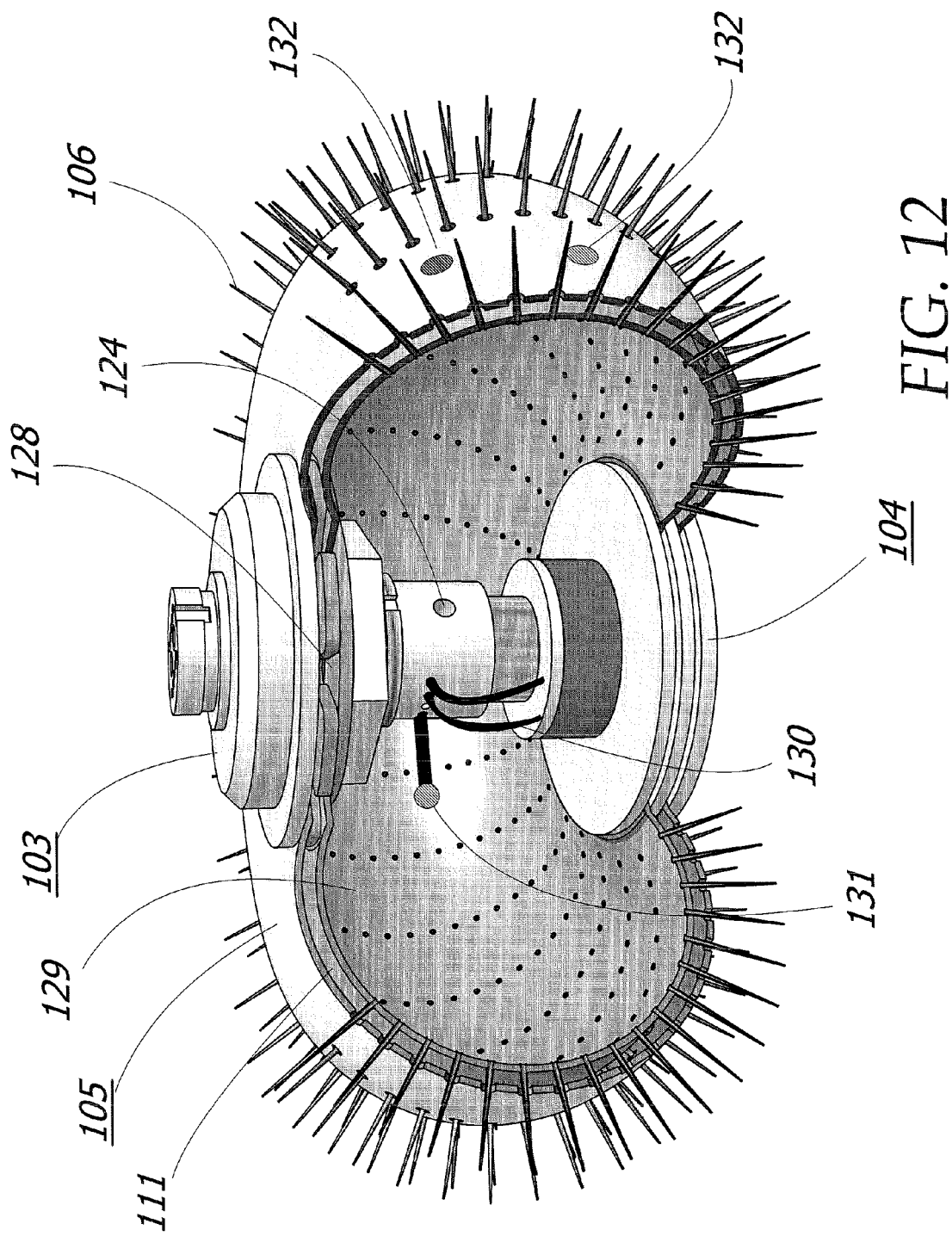
FIG. 12 is a cross sectional view of the implantable cranium pump.
Figure 13C:
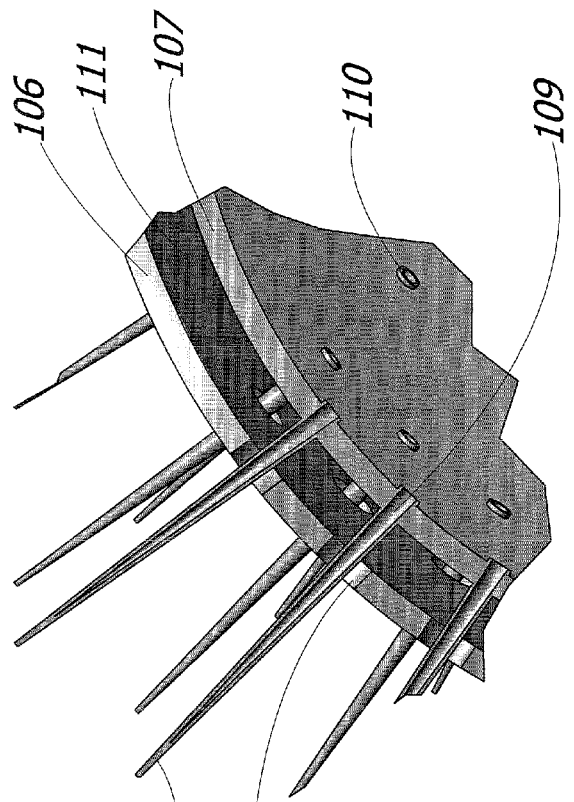
FIG. 13c is a magnified cross sectional view of the inner and outer membranes of the implantable cranium pump.

The implantable cranium pump unit 100 of the illustrated embodiment of the invention depicted in FIG. 10a comprises of two distinct polymer layers; an inner membrane 107 and the outer membrane 106 as best seen in FIG. 13c. Inner membrane 107 and outer membrane 106 are seamed together at the base and head of cranium pump 100 by a pump solenoid assembly 104 and a pump head assembly 103 respectively (FIG. 12). The pump solenoid assembly 104 and pump head assembly 103 provide a means for contracting and expanding the cranium pump 100 and are further discussed in more detail below. Both inner membrane 107 and outer membrane 106 are made from a skin-like polymer material. This material allows the pump 100 to be highly flexible during the drug delivery process and decreases the chances for infection or rejection from the body of a patient.

The space enclosed by inner membrane 107 is a medication reservoir 129 used for storing a medicating agent or a mixture of medicating agents as shown in FIG. 12. The size and volume of the medication reservoir 129 and thus the cranium pump 100 itself may be varied from patient to patient. A physician will make a determination of how much medication a particular patient will need and then the size of the medication reservoir 129 will be made accordingly. For example, a patient that needs large doses of medication will receive a cranium pump 100 with a larger medication reservoir 129 then a patient who only requires a small dose.

Figure 13A:
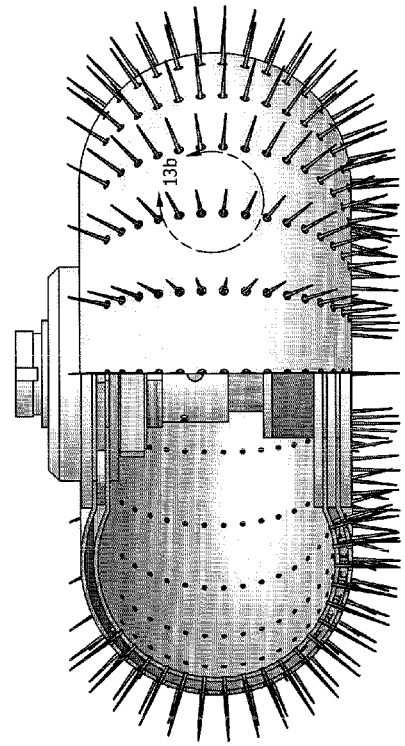
FIG. 13a is a partially cutaway cross sectional view of the implantable cranium pump with a polarity of injector spines highlighted.
Figure 13B:
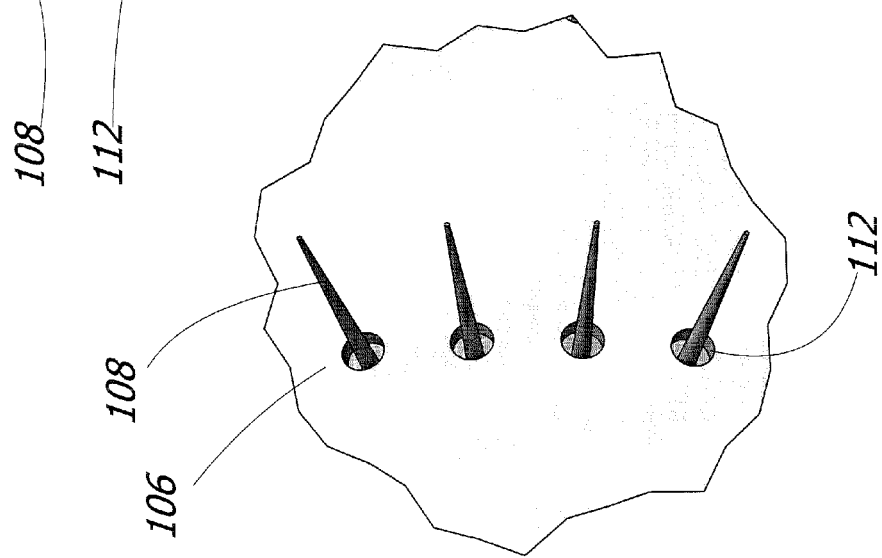
Figures 14A, 14B:
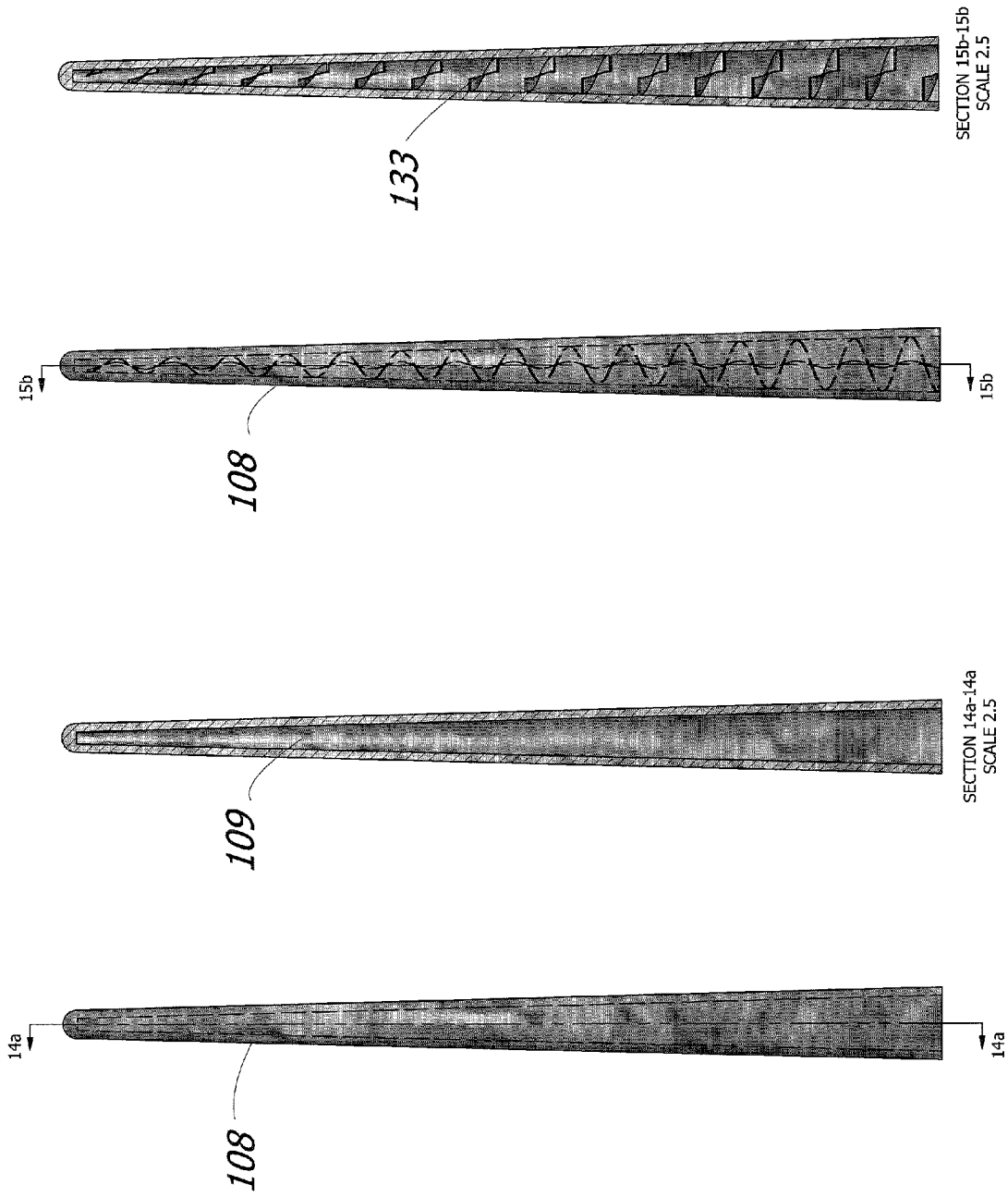
FIG. 14a is a side and cross sectional view of a hollow injector needle.
FIG. 14b is a side and cross sectional view of a spiral injector needle.

Turning again to FIGS. 13a-13c, the inner membrane 107 further comprises a plurality of small injector spines 108 distributed throughout the entire surface of the inner membrane 107. As can be seen in FIGS. 14a and 14b, the injector spines 108 may be comprised of hollow tubes 109 or a spiral design 133 with a pleated inlet 110 at its base where spine 108 meets the inner membrane 107 (FIG. 13c). The inner membrane 107 has a shape memory which effectively causes it to act as telescoping springs to rapidly extend and retract the injector spines 108 through the surface of the outer membrane 106. The injector spines 108 are also sufficiently long enough to penetrate the outer membrane 106 when the cranium pump 100 is in its most expanded state as shown in FIG. 10a. The injector spines 108 are tapered at their tips so that fluid flows substantially in only one direction, namely from the medication reservoir 129 to the surrounding tissue of the patient.

When the cranium pump 100 is being contracted or is in its supply stroke, the inner membrane 107 is pushed outward thus extending the injector spines 108 further past the outer membrane 106 and deeper into the patient's surrounding tissue. This process allows the pump 100 to deliver medicating agents deeper into the affected tissue and thus the tumor itself in a more direct way than any prior art method. The injector spines 108 extend into the patient's tissue and the increased pressure created by the contracting cranium pump 100 pushes the medicating agent out through the injector spines 108 at its most extreme extension point.

When the cranium pump 100 is expanding or is in its intake stroke, the inner membrane 107 collapses back to its original shape and thus retracts the injector spines 108 to their original position just outside of the outer membrane 106. When the injector spines 108 are retracted, the pressure differential of the cranium pump 100 will necessarily draw in a small amount of surrounding cerebral fluid into a sampling cavity 111. This is deemed beneficial however since the cerebral fluid will be eventually mixed with the medicating agent and thus increasing the diffusion rate of the medicating agent when it is pushed out of the injector spines 108 in any of the subsequent supply strokes. This process of extending and retracting the injector spines 108 is repeated for as long as the cranium pump 100 is activated.

Returning to FIG. 13c, the outer membrane 106 further comprises a plurality of micro pores 112 distributed throughout its entire surface. When the pump 100 is in the intake stroke, cerebral fluid is drawn into the pump 100 through the micro pores 112 due to the pressure differential that exists between the inside of pump 100 and the surrounding area outside of the pump 100. The amount of cerebral fluid that is drawn through the micro pores 112 is kept separated from the medication reservoir 129 by the inner membrane 107 and the lower portions of the injection spines 108. The volume of cerebral fluid that is then contained between the inner membrane 107 and outer membrane 106 then forms a sampling cavity 111. The components of cranium pump 100 is preferably composed of silicone, as this is the material currently used for ventriculoperitoneal shunts. However additional materials such as biodegradable material or other composites may be used without departing from the original spirit and scope of the invention.

Figures 15A, 15B:
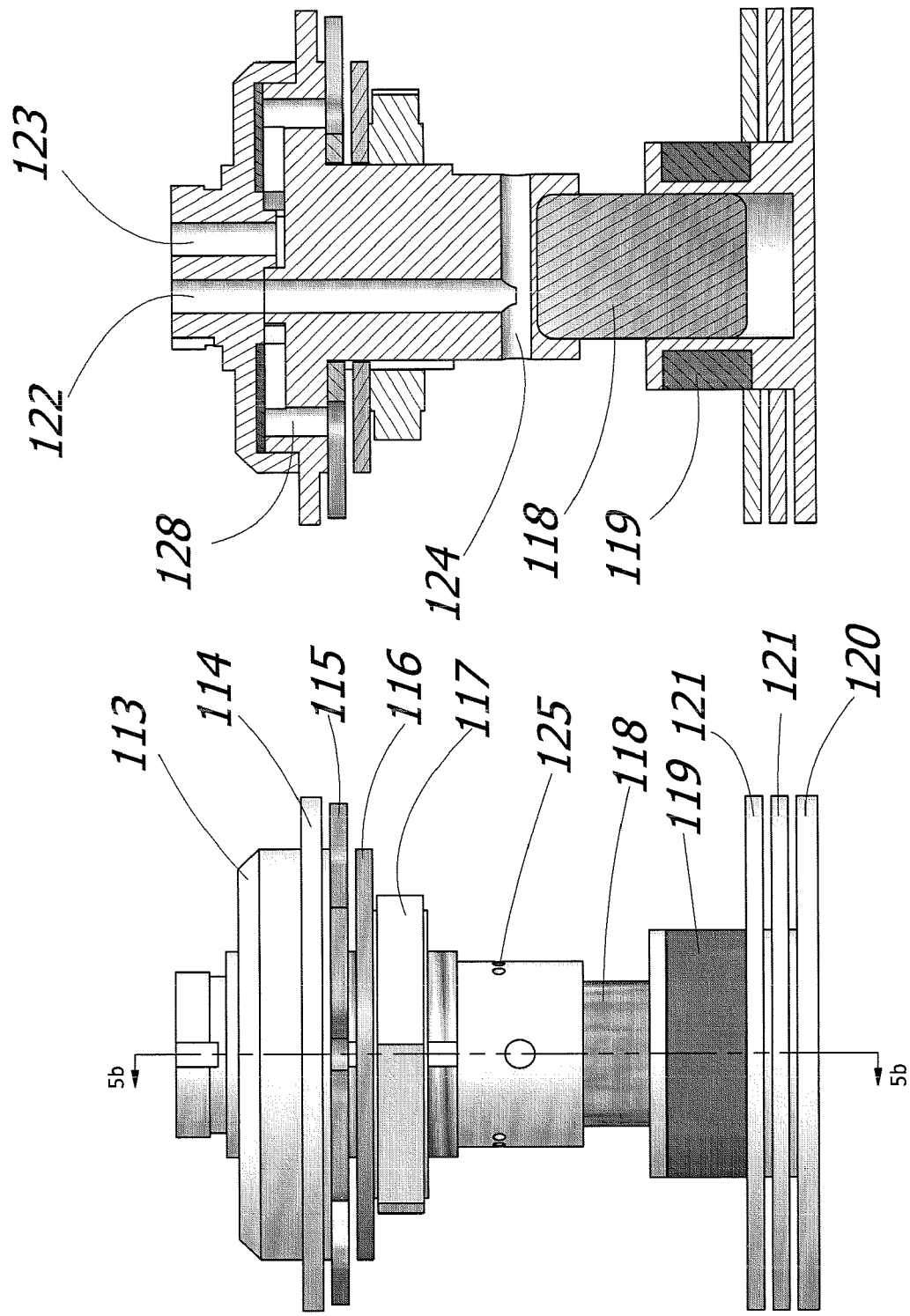
FIG. 15a is a front view of the pump actuator assembly.
FIG. 15b is a cross sectional view of the pump actuator assembly.

The detailed parts of the pump head 103 and pump solenoid 104 assemblies are shown in FIGS. 15a-16b. In FIG. 15a, the assembly is comprised of a coil 119 which can generate magnetic fields either reinforcing or opposing the magnetic field of a permanent magnet 118. The permanent magnet 118 is made of NbFe35 ceramic material however other materials may be used without departing from the original scope and spirit of the invention. The coil 119 may then be pulled or pushed away from the permanent magnet 118 depending on the current polarity of the coil 119. The coil 119 is coupled to a bobbin 120 and is constructed from a plurality of small (40 AWG) windings. The bobbin 120 is composed of several layers of bobbin washers 121. Because bobbin 120 is attached to the flexile skin-like material of the inner membrane 107, the coil 119 movement translates into an increase or decrease of pressure on the medication reservoir 129.

Controlling the amount of electrical current that passes through the coil 119 produces variable and regulated medication pressure which in turn adjusts the amount of medicating agent passing through a plurality of injector spines 108 described above. Conversely, the controlled movement of the coil 119 acts as a pumping function serving to provide suction to the outer membrane 106 of the pump and thus draw in surrounding cerebral fluid from the patient.

The apparatus uses a method similar to respiration to not only pump drugs into the brain, but also to sample the immediate area by creating a negative pressure in the sampling cavity 111. As can be seen in FIG. 12, the pump solenoid 104 and pump head 103 use a magnet 118 and coil 119 as a solenoid to create attraction or repulsion between the pump head 103 and the bobbin 120. This motion is then translated to the cranium pump 100. The outer membrane 106 is made of a more ridged durra silicon rubber than the inner membrane 107. When the pressure is reversed by the pump solenoid 104, because the inner membrane 107 is softer than the outer membrane 106, the gap between the membranes increases and the negative pressure sucks in the cerebral fluids through the aspirator micro-pores 112 around the spines 108 on the outer membrane 106. Turning back to FIGS. 15a and 15b, this sample fluid then gets removed between a sampling washer 115 through sampling collection ducts 128 in a delivery/sampling head 114 and out through a connector plate 113.

The connector plate 113 has both a drug inlet 122 and a sampling tube 123 connection. The connector plate 113 also comprises all the electrical connections for the coil 119, the pressure sensor 131 (shown in FIG. 12) and the temperature sensors 132 (also shown in FIG. 12). The top of drug inlet 122 and the sampling tube 123 as well as various sensor and coil connections can be seen in FIG. 11b.

Figure 16A:
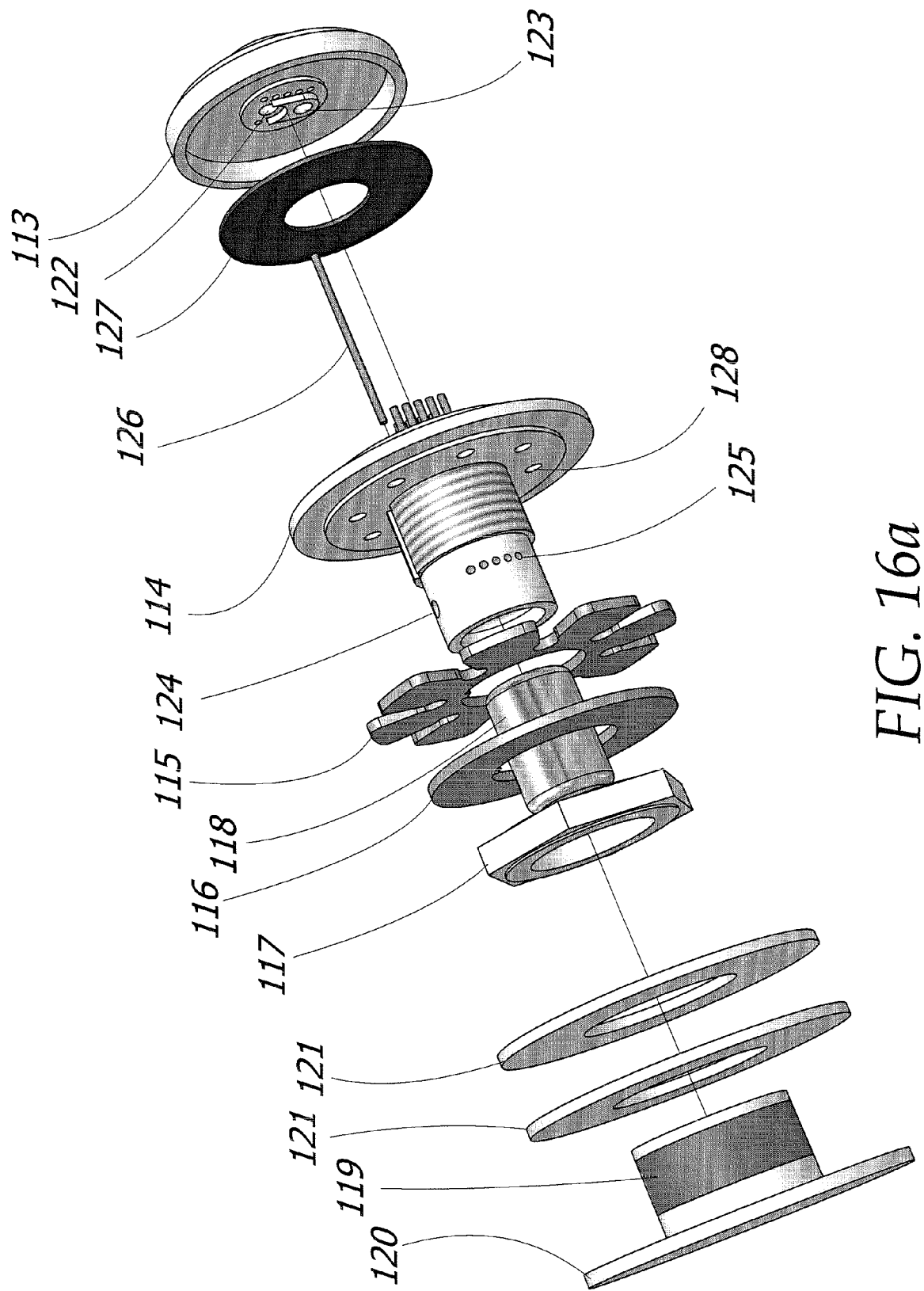
FIG. 16a is an exploded bottom view of the pump actuator assembly.
Figure 16B:
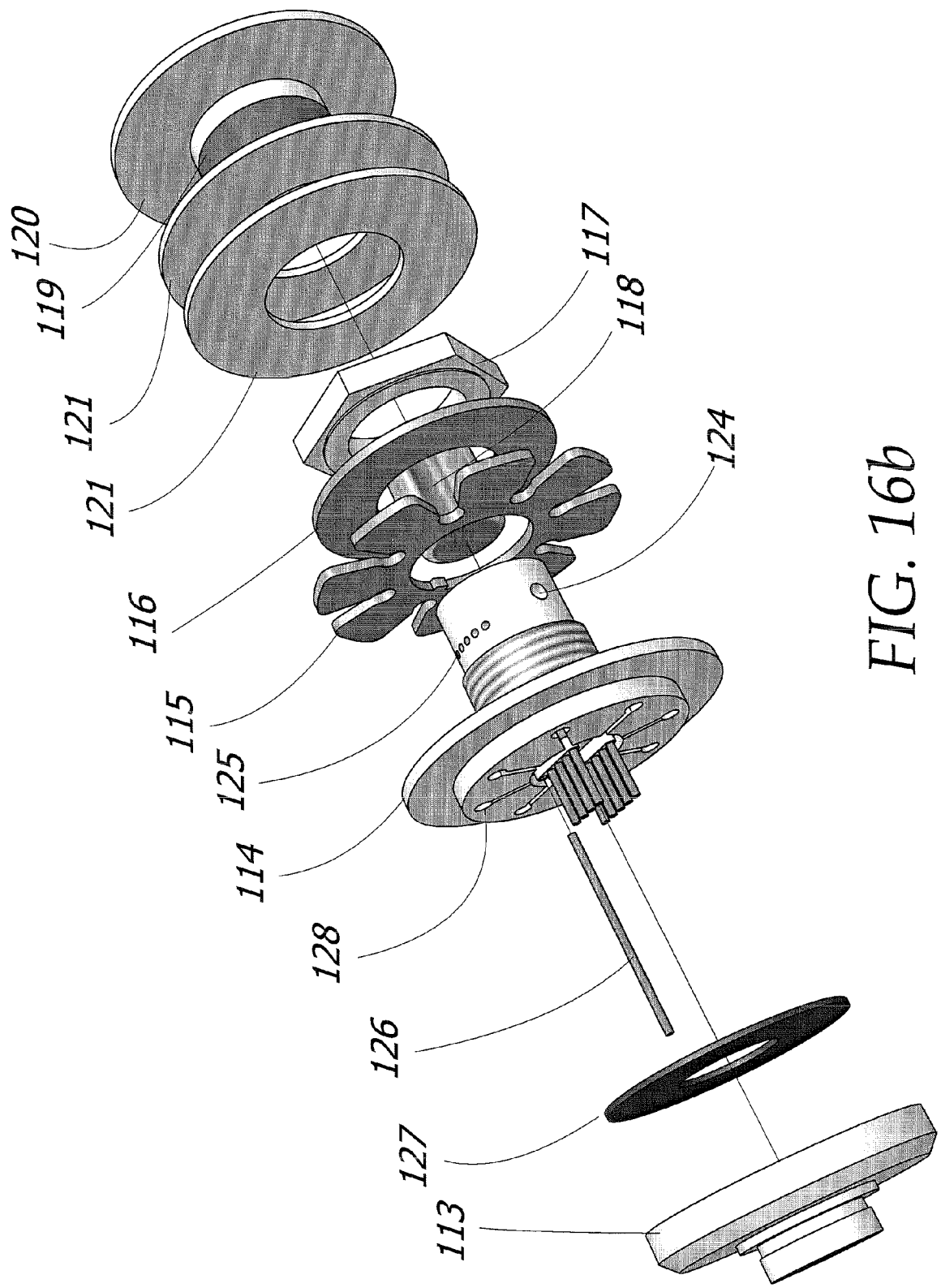
FIG. 16b is an exploded top view of the pump actuator assembly.

FIGS. 16a and 16b best show that the electrical connections are transferred through a series of sensor and coil pins 126 through the delivery/sampling head 114 to a plurality of sensor and coil connections 125 in the inner medication reservoir 129. Connections to the coil 119 are made with insulated flexible wire 130 (shown in FIG. 12).

Turning back to FIGS. 16a and 16b, the inner and outer membranes 107, 106 are attached and compressed by washers 121 to the bobbin 120. The bobbin 120 freely travels over the permanent NdFeB magnet 118. The magnet 118 is permanently coupled to the delivery/sampling head 114. The inner and outer membranes 107, 106 are also coupled directly to the delivery/sampling head 114. The sampling washer 115 and the bobbin 120 also provide the necessary gap of 0.020 inch for the medication reservoir 129. A compression nut 117 compresses an inner membrane washer 116 to clamp the inner membrane 107 against the delivery/sampling head 114. As seen in FIG. 15b, the delivery/sampling head 114 also comprises a drug dispersion tube 124 which releases the medicating agent or mixture of medicating agents to be administered to the patient into the medication reservoir 129.

Turning back to FIG. 10a, at the head of the cranium pump 100, the pump head assembly 103 located there is coupled to a seal connector 102 via a series of fluid lines and electronic connections enclosed in a pump-to-seal interconnect 101. The seal connector 102 is essentially a valve that controls the amount of fluid that is permitted to enter or leave the pump 100. When more medicating agent is needed, the seal connector 102 opens and allows the medicating agent to travel through the pump-to-seal interconnect 101 and enter the medication reservoir 129 below. When the correct amount of medicating agent has been applied, the seal connector 102 closes and all incoming fluid flow stops. Additionally, the seal connector 102 houses a suction nozzle (not shown) that applies suction to the sampling cavity 111 and draws up recently acquired cerebral fluid up and out of the pump 100 and through the seal connector 102.

Figure 10B:
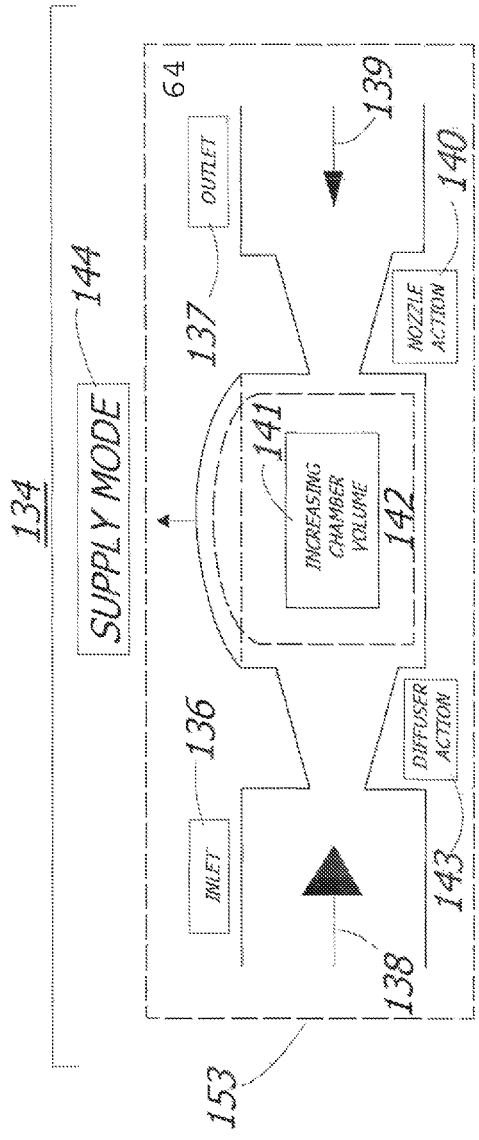
FIG. 10b is a diagram which depicts the "electrostatic muscle" defining the "supply mode" of the implantable cranium pump.
Figure 10C:
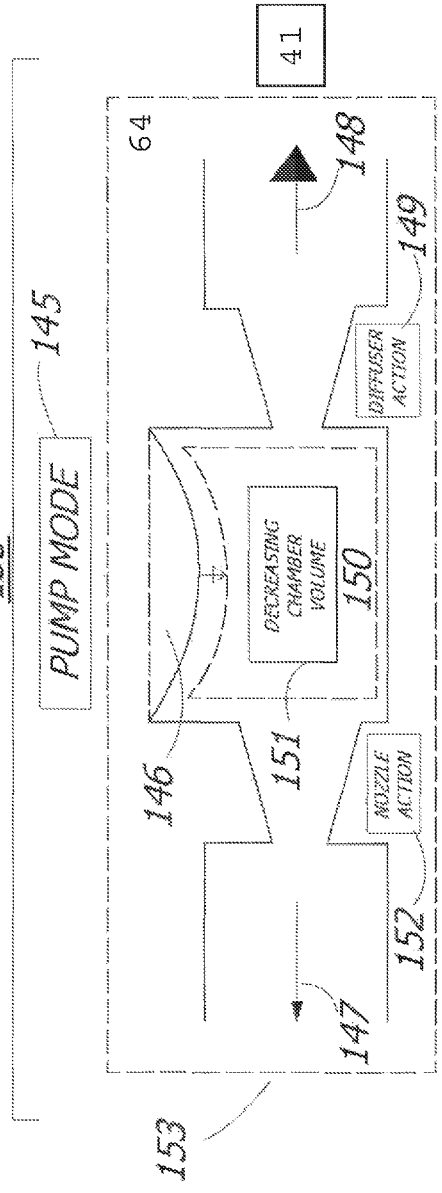
FIG. 10c is a diagram which depicts the "electrostatic muscle" defining the "pump mode" of the implantable cranium pump.

FIGS. 10b and 10c further depict the pump mode 145 and supply mode 144 as it is employed by the cranium pump 100. FIG. 10b and 10c depict the electrostatic muscle 64 in its closed state 134 which is also the supply mode 144, where the medicating agent or BRM are pumped out and transported from the cranium pump 100 to the desired tumor site or biological tissue of interest.

In FIG. 10b, the inlet nozzle is shown as 136, while an increasing chamber volume 141 is taking place. The increase in chamber volume causes flow 138 from the inlet 136 to enter the chamber 142 and at the same time, there is a small amount of fluid which flows from the outlet 137 into the chamber 142 as well. However, because of the venturi action of the inlet 136 and the outlet 137, the total net flow is from the cranium pump 100 into the chamber 142. In this case, the inlet 136 exhibits a diffuser action 143 and the outlet 137 exhibits a nozzle action 140.

FIG. 10c exhibits the electrostatic muscle 64 in its open state 135, which is also the pump mode 145. In this case there is a decrease in chamber volume 151, which causes a net flow to take place from the chamber 150 to the tumor site 41 through the outlet 148. Although there is a small amount of flow 147, from the chamber 150 to the inlet, the net flow is substantial and is from the chamber 150 to the tumor site 41. In this mode, the inlet 147 exhibits a nozzle action, 152 and the outlet exhibits a diffuser action 149.

Figure 1A:
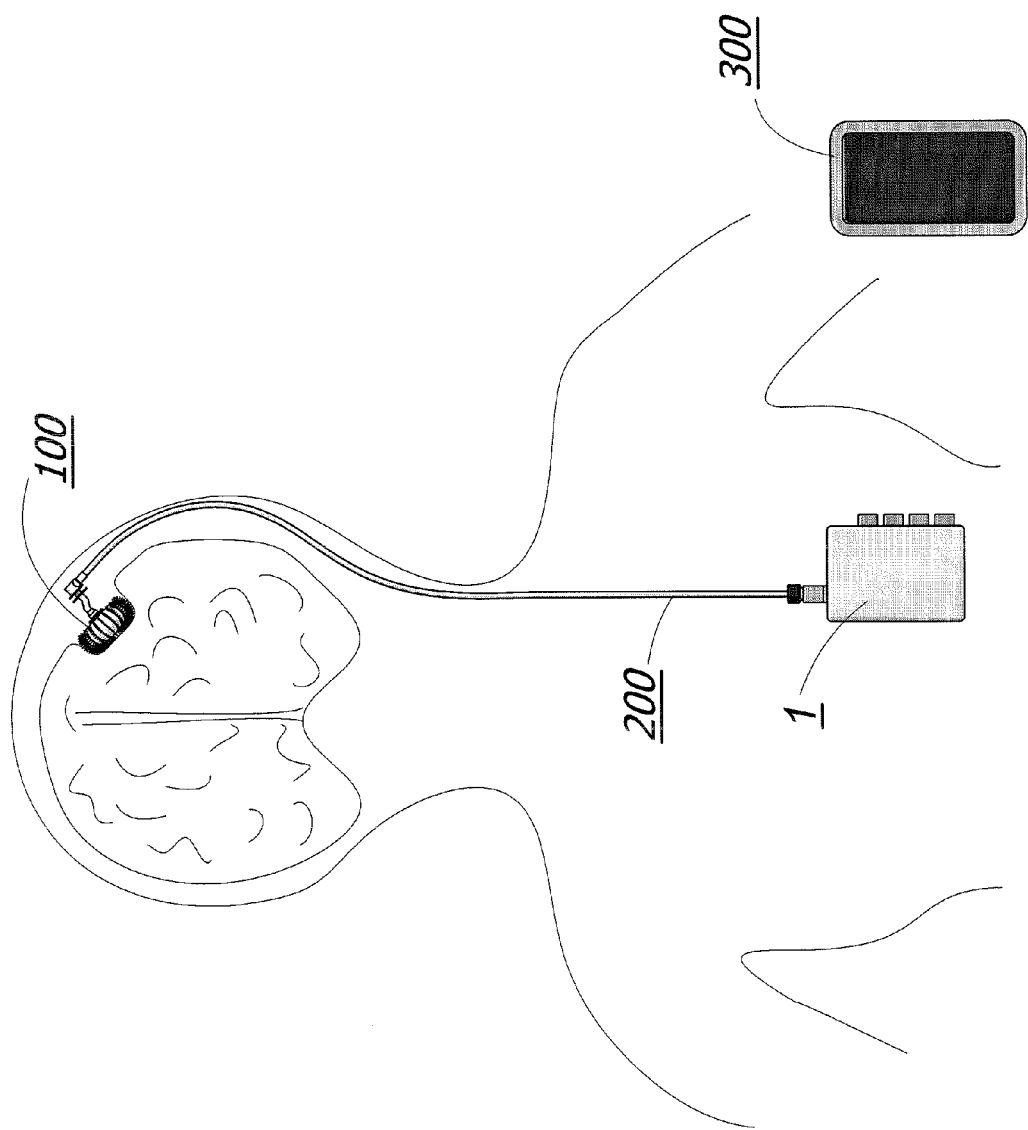
FIG. 1a is a diagrammatic cross sectional view of a patient's body after the implantable pump unit has been successfully implanted into the tumor cavity and placed under the patient's skull and dura and the CPD has been implanted beneath the skin in the chest cavity.

Turning to FIG. 1a, a delivery hose 200 is coupled to the seal connector 102 and a CPD 1 portion of the apparatus. The delivery hose 200 thus serves as a conduit between the pumping and analyzing portions of the current invention, and houses a refill line, a return sample fluid line, and several electronics connections for various sensors and the coil 119.

After the cranium of the patient has been opened and the skull and dura have been successfully breeched, the tumor, or as much of the tumor as possible, is removed. The soft cranium pump 100 is then placed in the resulting cavity, and the skull cap is reattached. As can be clearly seen, the pump 100 is positioned on the patient's brain beneath both the dura and skull of the patient. The seal connector 102 is coupled to pump 100 and is firmly embedded within the dura of the patient with the top portion of the shunt protruding from the skull. The delivery hose 200 is coupled to the seal connector 102 and leads away from the pump 100 and down the back of the neck of the patient underneath the skin. The delivery hose 200 lies beneath the scalp of the patient for the entire distance between the seal connector 102 and the point where the catheter is connected to the analyzer 1 at the clavicular head. The purpose for maintaining the catheter 200 beneath the scalp is to give the patient a sense of normalcy and confidence while they are undergoing treatment.

FIG. 1b shows an external data 300 logger which communicates with the chemotherapy pump device (CPD) 1. The CPD 1 communicates with the external controller 300 by the use of RF transmitter 304 and its associated antenna 302 and RF receiver 303 with its associated antenna 301. After implantation of the CPD 1 subcutaneously inside the patient 39, the system allows for programmability of the device in order to dispense the medicating agent in proper intervals over time and in the prescribed doses. Once the CPD 1 and cranium pump 100 is implanted and is in operation, the clinician may decide to change the parameters of the operation such as the amount of medication dispensed onto the tumor site or the time intervals associated with the dispense process. The clinician communicates with the internal electronics of CPD 1 using an external programming device 300 shown in FIG. 1b, which may be in the form of a desktop computer or any other similar appropriate device. The device 300 is able to communicate with the microcontroller in CPD 1 through its own microcontroller 305 via RF transmitter 304, its antenna 302, and the RF receiver 303 and its antenna 301, or via the serial communication port 307, located in the external control box 300. The new sets of commands are then transferred to the cranium pump 100. These new command data are then stored in the memory of the microcontroller of CPD 1, which is now programmed anew to perform the procedure as coded in the new instruction set.

The microcontroller located in CPD 1 and implanted inside the patient's body 39 communicates with the external control 300 via RF transmitter 304 and RF receiver 303 thereby sending its collected data to the external data logger 300. This feature enables the clinician to collect data and to determine the state of the patient throughout the period of treatment. These data are stored inside the external controller 300 providing chart history of the treatment status of the parameters associated with the tumor site. The CPD 1 transmits data for collection and storage. The data logger 300 is controlled by the user via the settings in control 308 and it also displays the amount of medicating agent dispensed over time by the cranium pump 100 on its display 309. Data collected in this manner can be used to correlate behavior pattern of a particular patient and his or her chart history. One can write a data collection and analysis program which can be displayed by the controller 300. Once the data are collected from the CPD 1, the external controller 300 or the host PC can then plot the data on a time scale and analyze the data further. It is significantly better to correlate between the input and the output or between cause and effect to mirror the action of the cranium pump 100 and its host tumor site. Such data in the form of historical plot of cause and effect benefit the patient 39 and aide in future research. The entire unit as shown in the figure is run by power obtained from its power source 306.

FIG. 1c is an illustration of a patient 39 with tumor of the form glioma with the implanted pump 100. The controller 300 with its associated serial port 307 and receiver and transmitter antennae 303 and 304 respectively is shown in its bidirectional communication model with the implanted CPD 1 via the RF path 310.

Figure 4B:
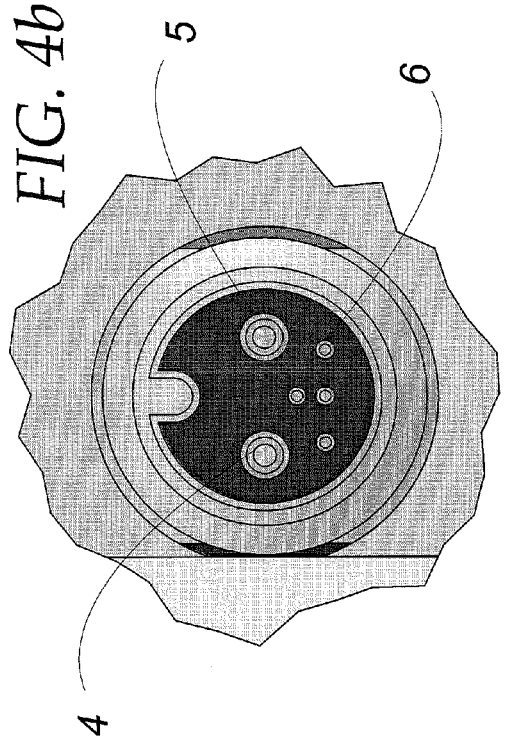
Figure 4D:
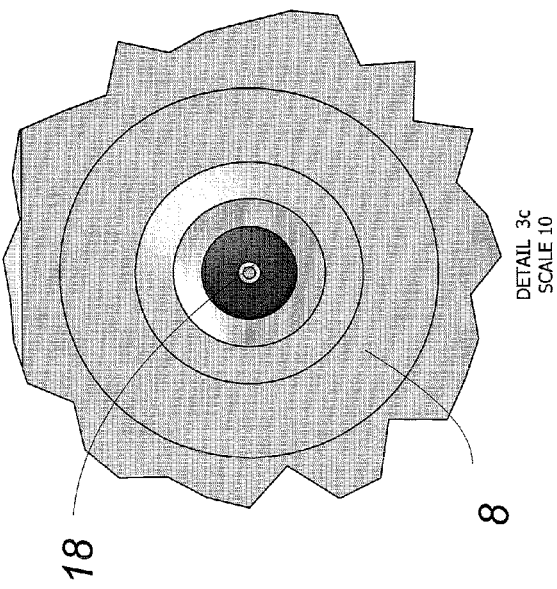
FIG. 4d is a magnified view of an ampoule bay of FIG. 4c.
Figure 4A:
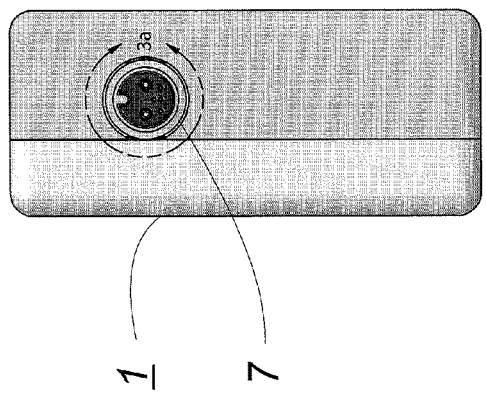
FIG. 4a is a right side view of the CPD highlighting the delivery connector.
Figure 4C:
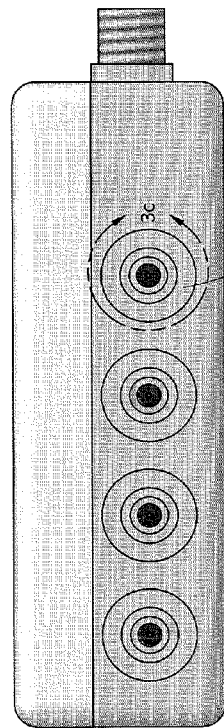
FIG. 4c is a bottom view of the CPD with an ampoule bay highlighted.

Turning to FIG. 4a, the CPD 1 comprises a delivery connector 7 where the delivery hose 200 couples with the CPD 1. The delivery connector 7 contains a drug outlet 4, a sample return 5, and a plurality of sensor connections 6 for controlling the pump unit 100 and for analyzing the sample fluid that is obtained from the cranium of the patient. The drug outlet 4 is the aperture in which medicating agents are sent from the CPD 1 through the delivery hose 200. Similarly, the sample return 5 is the aperture where cerebral fluid that has been collected by pump 100 is returned by the delivery hose 200 and enters the CPD 1 for analysis. The process by which the external CPD 1 sends medicating agents and receives sample fluid obtained from the patient through the delivery hose 200 is explained in further detail below.

Figure 2:
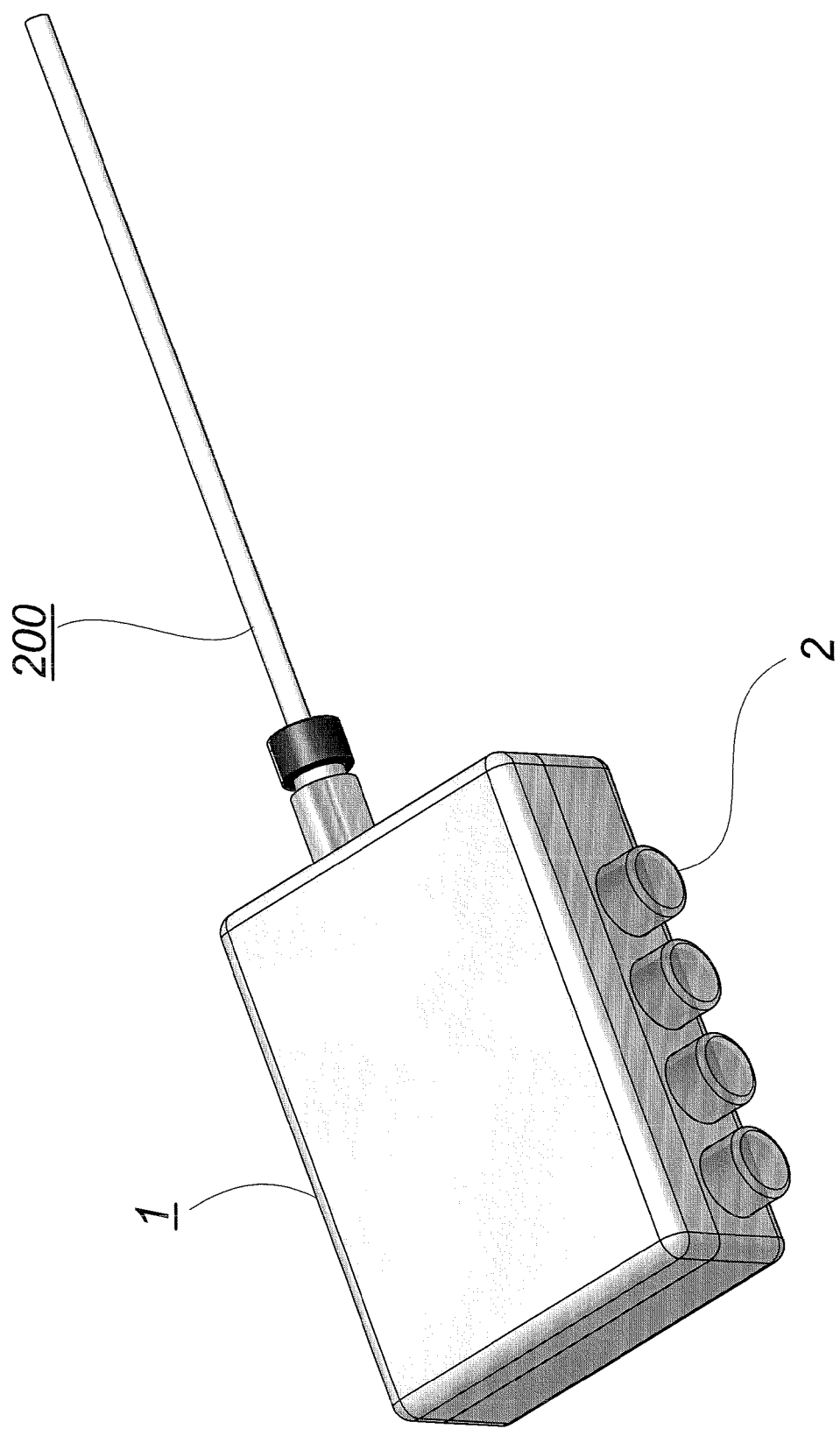
FIG. 2 is an isometric view of the CPD.
Figure 3C:
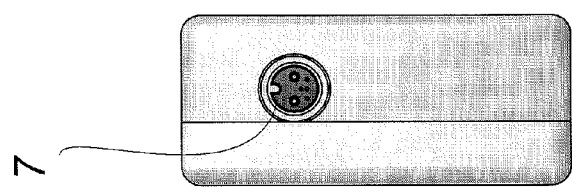
FIG. 3c is a right side view of the CPD.
Figure 3A:
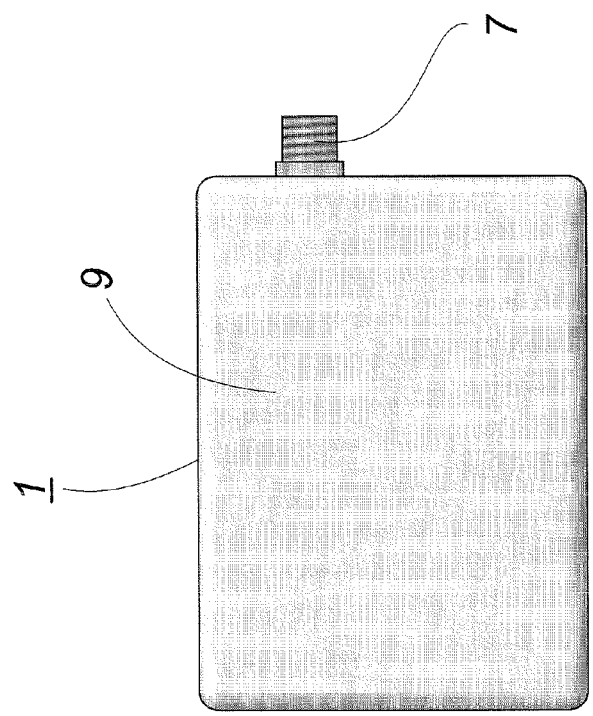
FIG. 3a is a front view of the CPD.
Figure 3B:
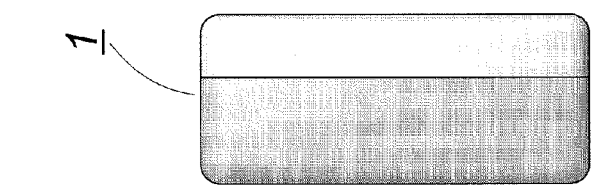
FIG. 3b is a left side view of the CPD.
Figure 3D:
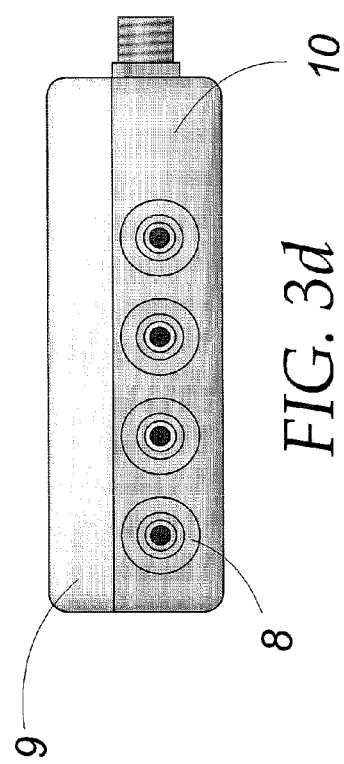
FIG. 3d is a bottom view of the CPD.

Up to four drug ampoules 2 (FIG. 2) can be deposed on the bottom portion 10 of the external CPD 1 in four separate ampoule bays 8 as depicted in FIG. 3d. It is to be expressly understood that fewer or additional ampoule bays may be present without departing from the original spirit and scope of the invention. To introduce a medicating agent into the CPD 1, a drug ampoule 2 is inserted into the ampoule bay 8. Drug needles 18 extending from the interior of the CPD 1 shown in FIG. 7a penetrate the ampoules 2 and carry the medicating agent. The CPD 1 then draws in the medicating agent in a series of steps that are described below.

Figure 6:
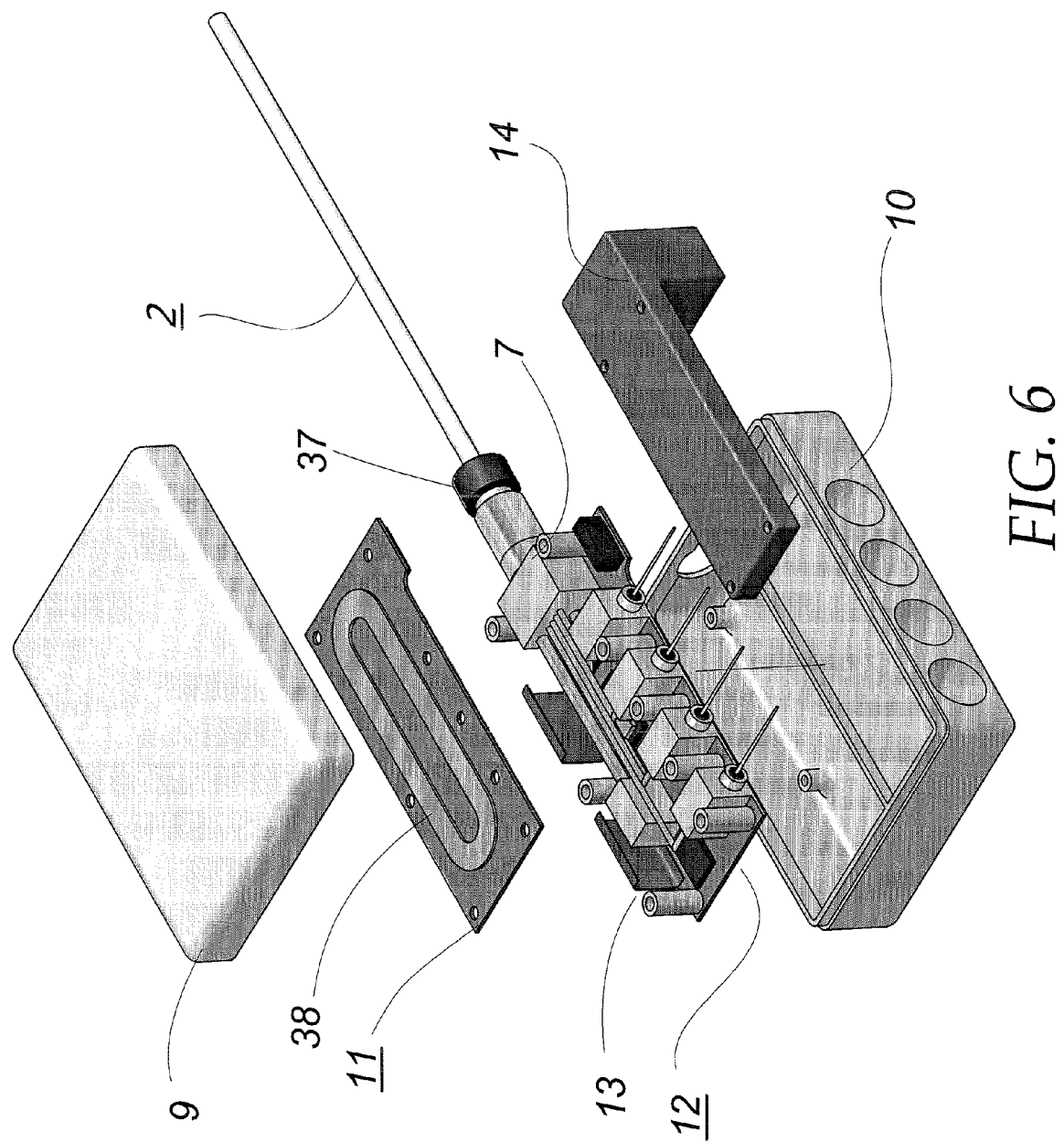
FIG. 6 is a fully exploded view of the CPD.
Figures 7A, 7B:
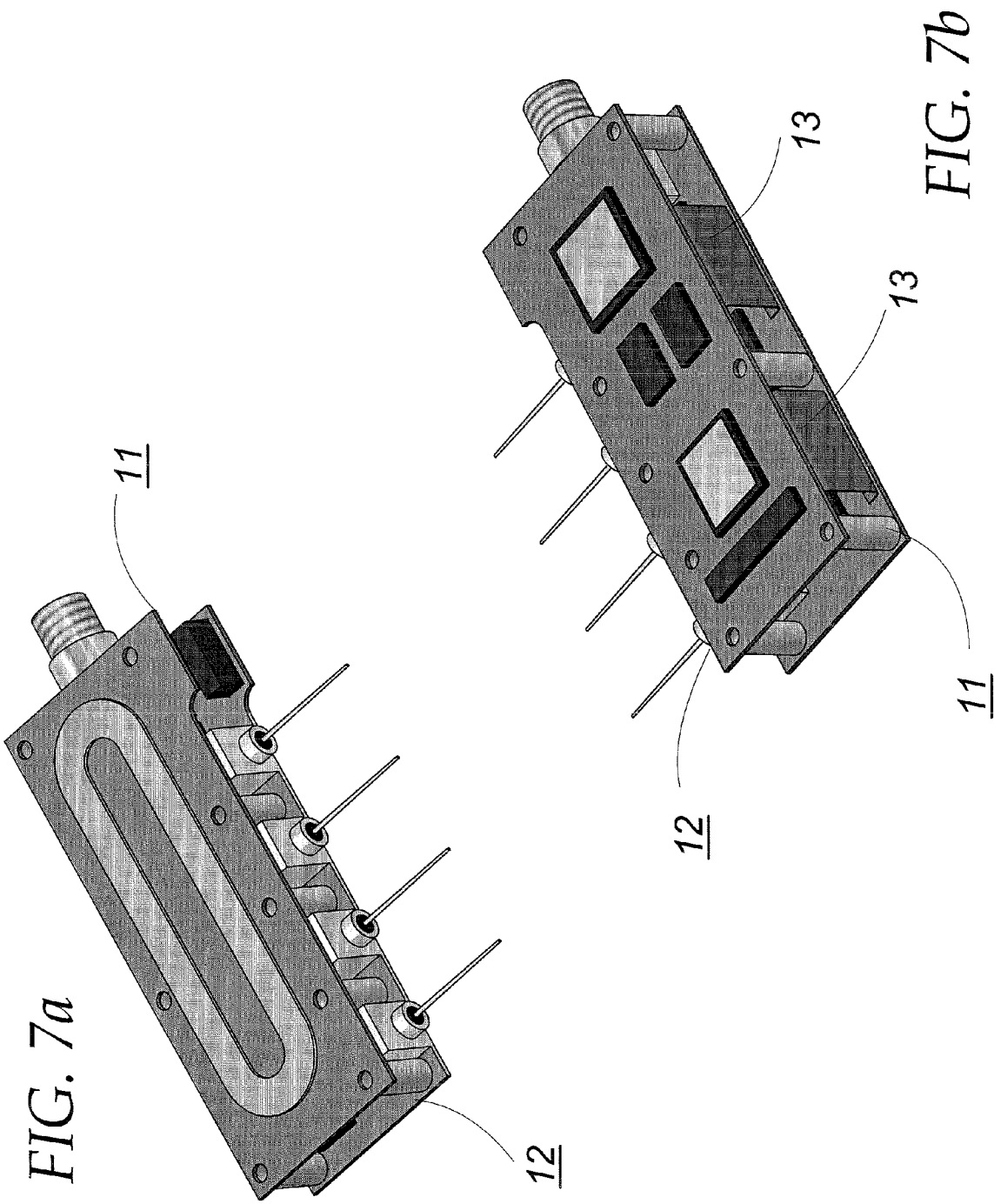
FIG. 7a is a perspective view of the top of the induction charger assembly and pump electronics assembly coupled together.
FIG. 7b is a perspective view of the bottom of the induction charger assembly and pump electronics assembly coupled together.

Turning to FIG. 6, the interior of the CPD 1 is comprised of two assemblies; a pump electronics assembly 12 and an induction charger assembly 11. The pump electronics assembly 12 and the induction charger assembly 11 are both housed within the external CPD 1 and are joined by an electronics interconnect cable 13 as best seen in FIGS. 7a and 7b.

Figures 8A, 8B:
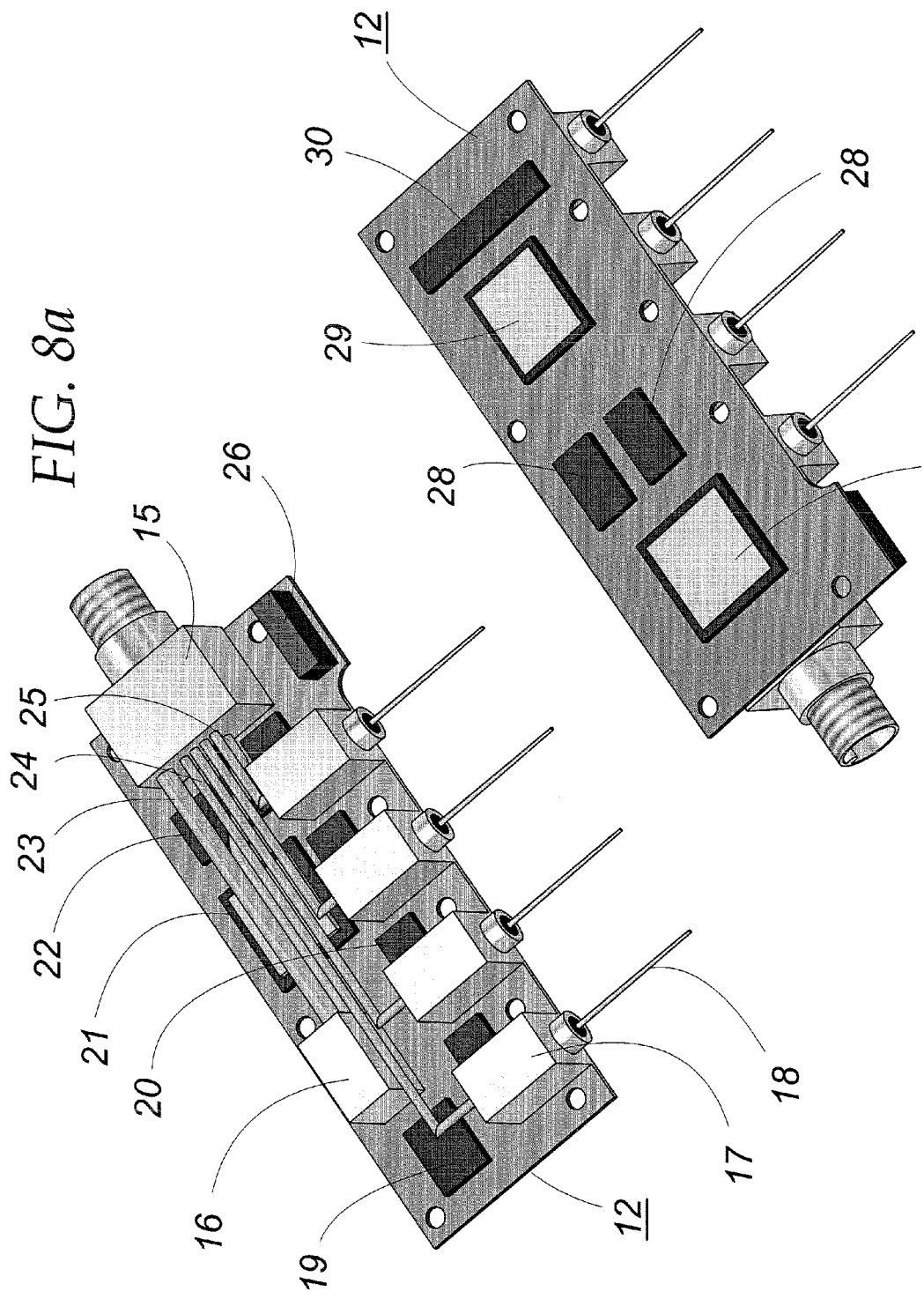
FIG. 8a is a perspective view of the top of the pump electronics assembly.
FIG. 8b is a perspective view of the bottom of the pump electronics assembly.

The pump electronics assembly 12 is shown in greater detail in FIGS. 8a and 8b. As seen in FIG. 8b, the pump electronics assembly 12 contains a drug delivery CPU 27 that stores its program and data into two FLASH memories 28. Pre-stored information such as look-up tables and the like are stored on the FLASH memories 28. The drug delivery CPU 27 runs a pre-installed intelligent chemo delivery software program and controls an ampoule pump integrated circuit 20, a return pump integrated circuit 19, and a delivery valve drift integrated circuit 22 as seen in FIG. 8a. The drug delivery CPU 27 also communicates with a lab-on-a-chip 21 and receives important treatment data such as sample temperature data through the sensor inputs 6 in the delivery connector 7 seen best in FIG. 6.

The drug delivery CPU 27 is pre-programmed and is capable of transmitting data through a Bluetooth® transceiver 29. The Bluetooth transceiver 29 is connected to a Bluetooth® antenna 30. A user or qualified physician who wishes to change the patient's drug regimen from a remote location first sends the data to the patient. The sent information is then picked up by the Bluetooth® transceiver 29 and antenna 30 and is then stored on the FLASH memory chips 28. When the drug delivery CPU 27 retrieves information from the FLASH memory chips 28 it adjusts the drug regimen (dose, scheduling, etc.) according to the user's data instructions.

Figure 5:
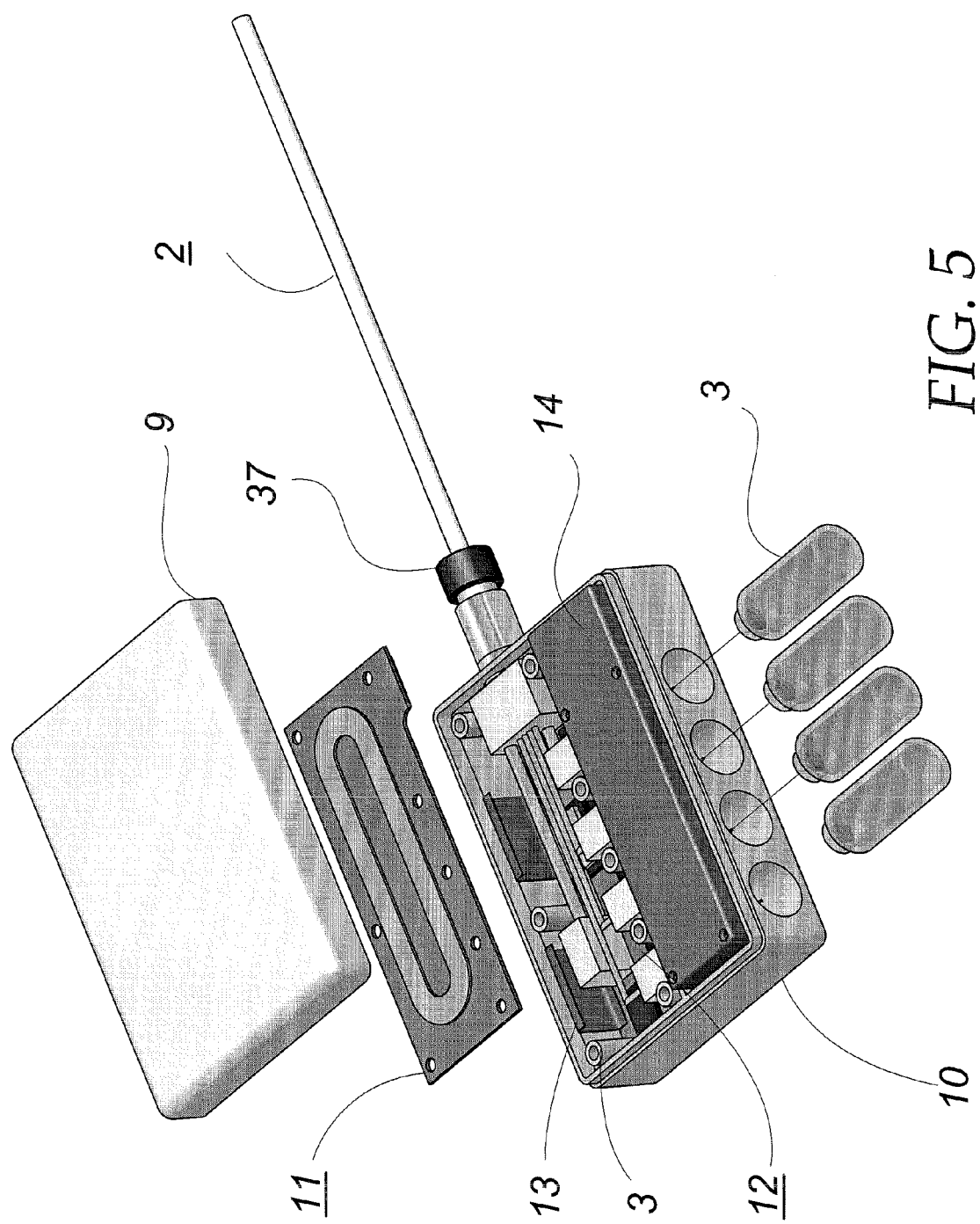
FIG. 5 is a partially exploded view of the CPD.

The external CPD 1 is capable of delivering up to four different drugs simultaneously with high accuracy in the following manner: The pump electronics assembly 12 of FIG. 8a comprises up to four piezoelectric pumps 17 driven by a corresponding ampoule pump integrated circuit 20 that together pump the medicating agent out of the ampoule 2. The use and manufacture of piezo pumps are well known to those in the art. Fewer or additional piezo pumps 17 than what is depicted in FIG. 8a may be used without departing from the original spirit and scope of the invention. The pump needles 18 are sufficiently long enough so that when a drug ampoule 2 is attached to the piezo pump 17 as depicted in FIG. 2, the medicating agent at the bottom of the ampoule may be accessed. Pump needles 18 coupled to the piezoelectric pumps 17 penetrate the ampoules 2 and the piezoelectric pump 17 pumps the medicating agent through a drug manifold tube 24 and into a delivery valve 15 and out through the drug delivery connector 7. The delivery valve 15 is regulated by a delivery valve driver integrated circuit 22 which is controlled by the drug delivery CPU 27. The medicating agent, after being pumped through the delivery connector 7, then enters into the delivery hose connector 37 (FIG. 5) via the drug output 4 on the delivery connector 7 depicted in FIG. 4b. The medicating agent is then pumped through the delivery hose 200 and into the cranial pump unit 100 via the seal connector 102. In FIG. 5, the delivery hose 200 couples to the CPD 1 via a delivery hose connector 37.

The external CPD 1 is fully programmable and runs intelligent software to determine what and how much drug is required. The regulation loop of the intelligent drug delivery system uses a return sample of fluids from the "delivery area" to determine the necessary response. In FIG. 5, the return sample fluid obtained from the patient travels through the delivery hose 200, through the delivery hose connector 37, and then enters delivery connector 7 through the sample return 5 as shown in FIG. 4b. Turning to FIG. 8a, after the sample fluid passes from the delivery connector 7, the sample fluid enters the delivery valve 15. The negative pressure necessary to pump the sample is created by the return piezoelectric pump 16 that is powered by a return pump driver integrated circuit 19. The fluid sample then travels from the delivery valve 15 into a return pump input tube 25 and into a lab-on-a-chip 21 that senses the chemical composition of the sample. The return piezoelectric pump 16 continues pumping the sample fluid through itself and back out into a return output pump tube 23. The sample fluid is then mixed together with the delivery drug in the delivery valve 15, to continue a closed loop cycle to be returned to the collection site.

The second main assembly, the induction charger assembly 11, is depicted in greater detail in FIGS. 9a and 9b. The induction charger assembly 11 provides with a means for charging a lithium ion battery 14 (shown in FIG. 5). An induction coil 38 coupled to the induction charger electronics assembly 11 receives a high frequency (50 Khz) induced magnetic field from a similar charging coil from an external battery charger device (not shown). The induction coil 38 is coupled to a rectifier 35 shown in FIG. 9b. The rectifier 35 converts the high frequency voltage to a DC voltage that is filtered by an inductor 34 and capacitors 33. A battery charger controller 32 regulates the charging of the battery 14. The charger connector 36 is both for powering the electronics as well as charging the lithium ion battery 14. The battery 14 is appropriately sized to provide sufficient power for days of service without the need of charging.

The lithium ion battery 14 preferably has an "L" shape as shown in FIG. 6 so as to leave sufficient space available for the pump needles 18 and drug ampoules 2 within the housing of the CPD 1 and is sized to provide sufficient power for days of service without the need of re-charging. However it is to be expressly understood that other varieties of batteries with various life spans and shapes may also be used without departing from the original scope and spirit of the invention. The lithium ion battery 14 is coupled directly to the housing of the CPD 1 and is removable so that when the stored energy has been depleted from the battery 14, it may be easily replaced.

Figure 17:
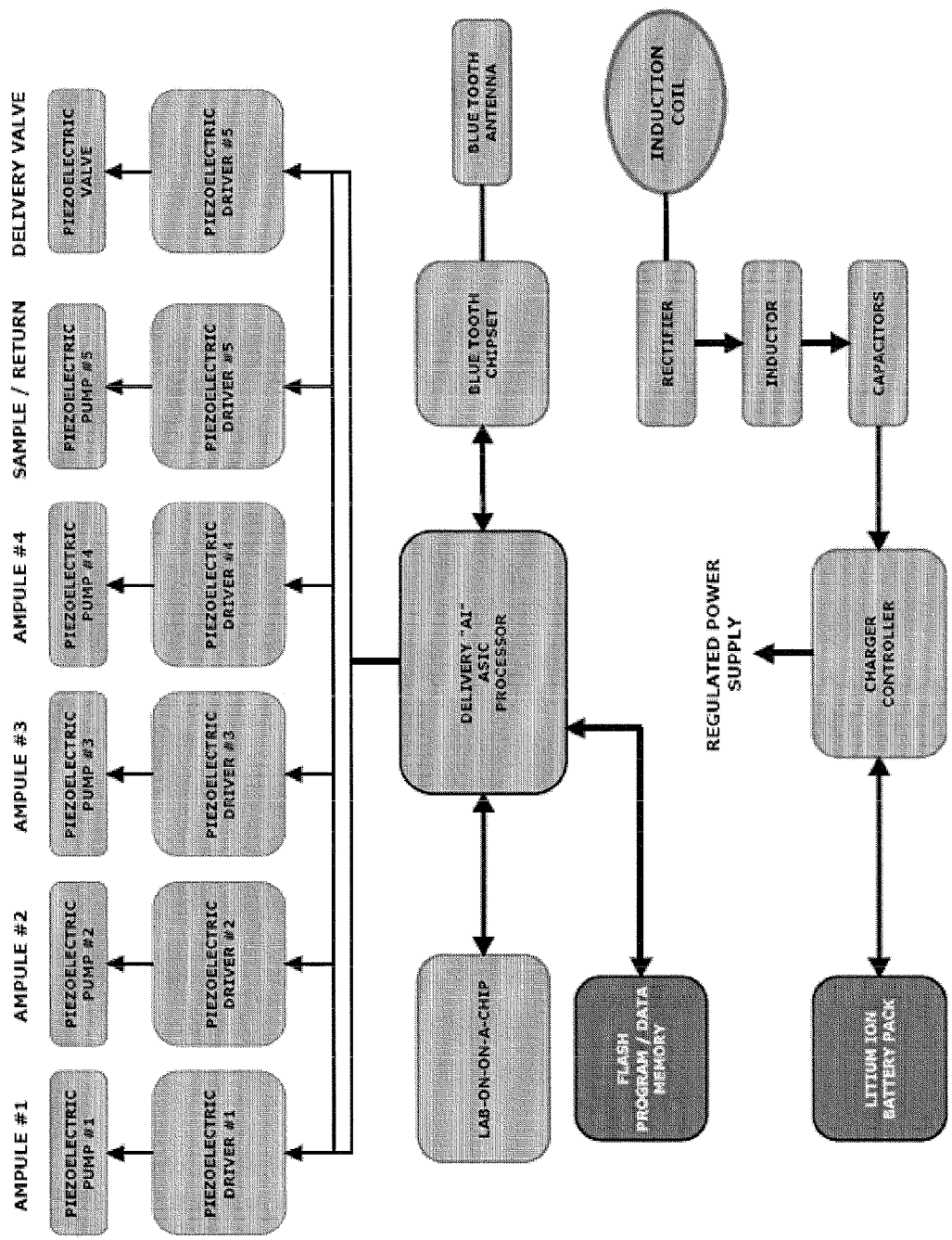
FIG. 17 is a functional block diagram of the pump actuator assembly.

FIG. 17 is a functional circuit diagram further illustrating the relationship between the elements of CPD 1 described above.

Many alterations and modifications may be made by those having ordinary skill in the art without departing from the spirit and scope of the invention. Therefore, it must be understood that the illustrated embodiment has been set forth only for the purposes of example and that it should not be taken as limiting the invention as defined by the following invention and its various embodiments.

For example, one skilled in the art may produce a device with fewer or additional drug ampoule bays or piezoelectric pumps without departing from the original scope and spirit of the invention.

Therefore, it must be understood that the illustrated embodiment has been set forth only for the purposes of example and that it should not be taken as limiting the invention as defined by the following claims. For example, notwithstanding the fact that the elements of a claim are set forth below in a certain combination, it must be expressly understood that the invention includes other combinations of fewer, more or different elements, which are disclosed in above even when not initially claimed in such combinations. A teaching that two elements are combined in a claimed combination is further to be understood as also allowing for a claimed combination in which the two elements are not combined with each other, but may be used alone or combined in other combinations. The excision of any disclosed element of the invention is explicitly contemplated as within the scope of the invention.

The words used in this specification to describe the invention and its various embodiments are to be understood not only in the sense of their commonly defined meanings, but to include by special definition in this specification structure, material or acts beyond the scope of the commonly defined meanings. Thus if an element can be understood in the context of this specification as including more than one meaning, then its use in a claim must be understood as being generic to all possible meanings supported by the specification and by the word itself.

The definitions of the words or elements of the following claims are, therefore, defined in this specification to include not only the combination of elements which are literally set forth, but all equivalent structure, material or acts for performing substantially the same function in substantially the same way to obtain substantially the same result. In this sense it is therefore contemplated that an equivalent substitution of two or more elements may be made for any one of the elements in the claims below or that a single element may be substituted for two or more elements in a claim. Although elements may be described above as acting in certain combinations and even initially claimed as such, it is to be expressly understood that one or more elements from a claimed combination can in some cases be excised from the combination and that the claimed combination may be directed to a subcombination or variation of a subcombination.

Insubstantial changes from the claimed subject matter as viewed by a person with ordinary skill in the art, now known or later devised, are expressly contemplated as being equivalently within the scope of the claims. Therefore, obvious substitutions now or later known to one with ordinary skill in the art are defined to be within the scope of the defined elements.

The claims are thus to be understood to include what is specifically illustrated and described above, what is conceptionally equivalent, what can be obviously substituted and also what essentially incorporates the essential idea of the invention.

We claim:

1. A method for treating a brain tumor in a patient comprising:

surgically implanting a cranium pump beneath the skull and dura of the patient's brain into a treatment site;

coupling the cranium pump to an analyzer unit disposed outside the patient's brain via a fluid exchange catheter;

operating the cranium pump within the brain of the patient in order to dispense a medicating agent to the treatment site under control of the analyzer unit;

suctioning in a sample of cerebral fluid from the treatment site and transferring it to the analyzer unit;

tracking and monitoring the progress of the patient's treatment via the analyzer unit;

altering and changing the patient's treatment proactively by controlling the analyzer unit via an external controller communicated to the analyzer unit by an RF link, the external controller allowing proactive alteration of a delivery schedule of medicating agents to the brain of the patient by the cranium delivery pump based on measurements of a plurality of tumor parameters obtained from the cranium delivery pump and quantified by the analyzer unit;

displaying the tumor parameter measurements on a display coupled to the external controller; and refilling and replacing a reservoir of medicating agent located in the analyzer unit, wherein suctioning the sample of the patient's cerebral fluid further comprises suctioning the sample cerebral fluid at a variable rate into an intra-membrane reservoir defined between an outer and inner membrane in the cranium pump by the oscillation of a magnetic solenoid and a plurality of pores defined within the surface of the outer membrane and around each distal tip of a plurality of hollow needles coupled to the inner membrane.

2. The method of claim 1 where operating the cranium pump comprises:

contracting and expanding a plurality of hollow needles fluidly coupled to an inner membrane reservoir in the cranium pump by oscillation of a magnetic solenoid;

extending the plurality of hollow needles through an outer membrane and an intra-membrane reservoir defined between the outer membrane and inner membrane reservoir when the inner membrane reservoir is being expanded;

retracting the plurality of hollow needles through the outer membrane and the intra-membrane reservoir defined between the outer membrane and the inner membrane reservoir when the inner membrane reservoir is being contracted such that the distal ends of the plurality of hollow needles do not retract past the outer membrane; and preventing any fluid communication between the inner membrane reservoir and the intra-membrane reservoir.

3. The method of claim 1 where tracking and monitoring the progress of the patient's treatment further comprises passing the sample of cerebral fluid through a lab-on-a-chip in the analyzer unit.

4. The method of claim 3 where passing the sample of cerebral fluid through a lab-on-chip further comprises displaying the results obtained from the lab-on-a-chip on a display.

5. The method of claim 1 where altering and changing the patient's treatment by controlling the analyzer unit further comprises entering command functions and data into the analyzer unit from a remote keypad and displaying the commands on a display.

6. The method of claim 5 where altering and changing the patient's treatment by controlling the analyzer unit further comprises sending command functions and data to the analyzer unit by means of a Bluetooth® transceiver and antenna.

7. The method of claim 1 where refilling and replacing the reservoir of medicating agent located in the analyzer unit further comprises refilling and replacing at least four drug ampoules coupled to the analyzer unit.

* * * * *